(12) United States Patent
Yun et al.

(10) Patent No.: US 7,899,527 B2
(45) Date of Patent: Mar. 1, 2011

(54) TREATMENT OF CONDITIONS THROUGH MODULATION OF THE AUTONOMIC NERVOUS SYSTEM DURING AT LEAST ONE PREDETERMINED MENSTRUAL CYCLE PHASE

(75) Inventors: Anthony Joonkyoo Yun, Palo Alto, CA (US); Patrick Yuarn-Bor Lee, Piedmont, CA (US)

(73) Assignee: Palo Alto Investors, Palo Alto, CA (US)

( * ) Notice: Subject to any disclaimer, the term of this patent is extended or adjusted under 35 U.S.C. 154(b) by 307 days.

(21) Appl. No.: 10/846,486

(22) Filed: May 13, 2004

(65) Prior Publication Data
US 2005/0256028 A1 Nov. 17, 2005

(51) Int. Cl.
*A61N 1/00* (2006.01)

(52) U.S. Cl. ............. 607/2; 607/1; 607/34; 607/30; 514/15.6

(58) Field of Classification Search ............. None
See application file for complete search history.

(56) References Cited

U.S. PATENT DOCUMENTS

| | | | |
|---|---|---|---|
| 4,888,343 A * | 12/1989 | Jones et al. | 514/263.31 |
| 5,188,104 A | 2/1993 | Wernicke et al. | |
| 5,215,086 A | 6/1993 | Terry, Jr. et al. | |
| 5,223,540 A * | 6/1993 | Wurtman et al. | 514/640 |
| 5,231,988 A | 8/1993 | Wernicke et al. | |
| 5,263,480 A | 11/1993 | Wernicke et al. | |
| 5,269,303 A | 12/1993 | Wernicke et al. | |
| 5,330,515 A | 7/1994 | Rutecki et al. | |
| 5,335,657 A | 8/1994 | Terry, Jr. et al. | |
| 5,540,730 A | 7/1996 | Terry, Jr. et al. | |
| 5,571,150 A | 11/1996 | Wernicke et al. | |
| 5,707,400 A | 1/1998 | Terry, Jr. et al. | |
| 5,716,377 A * | 2/1998 | Rise et al. | 607/2 |
| 5,978,702 A | 11/1999 | Ward et al. | |
| 6,253,109 B1 | 6/2001 | Gielen | |
| 6,319,241 B1 | 11/2001 | King et al. | |
| 6,337,997 B1 | 1/2002 | Rise | |
| 6,356,784 B1 | 3/2002 | Lozano et al. | |
| 6,366,813 B1 | 4/2002 | DiLorenzo | |
| 6,459,936 B2 | 10/2002 | Fischell et al. | |
| 6,480,743 B1 | 11/2002 | Kirkpatrick et al. | |
| 6,484,059 B2 | 11/2002 | Gielen | |
| 6,526,318 B1 | 2/2003 | Ansarinia | |
| 6,609,025 B2 | 8/2003 | Barrett et al. | |
| 2002/0177882 A1 | 11/2002 | DiLorenzo | |
| 2002/0188336 A1 * | 12/2002 | Bothe Loncar et al. | 607/96 |
| 2003/0018367 A1 | 1/2003 | DiLorenzo | |
| 2003/0144709 A1 | 7/2003 | Zabara et al. | |

OTHER PUBLICATIONS

Wikipedia definitions accessed Jun. 14, 2006: wikipedia.org/wiki/Sympathetic_nervous_system; p. 1-2.*
Wikipedia definitions accessed Jun. 14, 2006: wikipedia.org/wiki/Parasympathetic_nervous_system; p. 1-2.*
Kaplan et al., Clin. Exp. Obstet. Gyn. 1994. XXI; 87-90.*
Wheatley, Psychotherapy and psychosomatics. 1988; 49: 63-80.*
Deligeoroglou, Annals of New York Acad Sci. 2000; 900: 237-244.*
Goldberger et al. Circulation. 2001; 103: 1977-1983.*
Romani et al., Journal of Women's Health; 12: 2003: 287-298.*
Krystal AD. Clin Cornerstone. 2004;6 Suppl 1B:S19-28.*
Pat Sonnenstuhl, May 1999, downloaded on Dec. 19, 2007 at: obgyn.net/print.asp?page=/yw/articles/pats_dysmenorrha; 5 pages.*
Email message regarding the date of availability of the Sonnenstuhl reference; 1 page.*
Website at obgyn.net/women/conditions/conditions.asp; 3 pages; downloaded Jan. 9, 2009.*
Kane et al., Am J Gastroenterol. 1998; 93: 1867-72.*
Zeitlin et al. J Clin Invest. Nov 20, 2008. [Epub ahead of print].*
Csapo, J Reprod Med. 1980; 25: 213-21.*
Dabrowska et al., Cardiology. 1996; 87(2): 119-24.*
Yun and Daniel, Medical Hypotheses, 2005; 65: 1172-1175.*
Nishimura et al., Biological Rhythm Research, 2003; 34: 233-240.*
Web archive dowloaded Jan. 11, 2010 from web.archive.org/web/19981203033132/http://www.midlife-passages.com/page121.html, which shows that this website was originally online Apr. 19, 1998; 6 pages total.*
Kanoa and Jih, Journal of Applied Physiology, 1975; 39: 801-805.*
Sato et al., Psychosomatic Medicine, 1995; 57: 331-335.*
Landen et al., Psychoneuroendocrinology, 2004; 29: 733-740.*
Baker et al., J. Psychosom Res. 2008; 65: 13-22.*
Matsumoto et al., International Congress Series, 2006; 1287: 323-328.*

* cited by examiner

*Primary Examiner* — Bridget E Bunner
*Assistant Examiner* — Christina Borgeest
(74) *Attorney, Agent, or Firm* — Bozicevic, Field & Francis LLP; Bret E. Field; Lynn J. Kidder

(57) ABSTRACT

Methods are provided for treating a subject for a condition. In accordance with the subject methods, at least a portion of a subject's autonomic nervous system is modulated during at least one predetermined phase of the subject's menstrual cycle to alter the parasympathetic activity/sympathetic activity ratio in a manner that is effective to treat the subject for the condition. The subject methods find use in the treatment of a variety of different conditions, including various disease conditions, that increase in severity and/or occurrence during one or more phases of the menstrual cycle. Also provided are systems and kits for use in practicing the subject methods.

29 Claims, No Drawings

TREATMENT OF CONDITIONS THROUGH MODULATION OF THE AUTONOMIC NERVOUS SYSTEM DURING AT LEAST ONE PREDETERMINED MENSTRUAL CYCLE PHASE

FIELD OF THE INVENTION

The field of this invention is the treatment of conditions associated with the autonomic nervous system and more specifically the treatment of conditions through modulation of at least a portion of the autonomic nervous system during at least one predetermined phase of the menstrual cycle.

BACKGROUND OF THE INVENTION

There are a variety of conditions that can affect a female's health and well-being. Certain conditions increase in severity and/or occurrence during one or more phases of a female's menstrual cycle. While the exacerbation of certain medical conditions during specific phases of the menstrual cycle has been recognized (commonly referred to as conditions that have catamenial variations), the mechanism underlying the association between exacerbation of medical conditions and certain menstrual phases is poorly understood.

Treatment options directed to treating these types of conditions have thus far failed to be wholly satisfactory. For example, since the causes are poorly understood, such options are typically merely palliative, i.e., are designed for the relief of symptoms of the condition rather than being directed at the cause.

As such, there continues to be an interest in the development of new protocol options for treating conditions that increase in severity and/or occurrence during one or more phases of a female's menstrual cycle.

SUMMARY OF THE INVENTION

Methods are provided for treating a subject for a condition. In accordance with the subject methods, at least a portion of a subject's autonomic nervous system is modulated during at least one predetermined phase of the subject's menstrual cycle to alter the parasympathetic activity/sympathetic activity ratio in a manner that is effective to treat the subject for the condition. The subject methods find use in the treatment of a variety of different conditions, including various disease conditions, that increase in severity and/or occurrence during one or more phases of the menstrual cycle. Also provided are systems and kits for use in practicing the subject methods.

DETAILED DESCRIPTION OF THE INVENTION

Methods are provided for treating a subject for a condition. In accordance with the subject methods, at least a portion of a subject's autonomic nervous system is modulated during at least one predetermined phase of the subject's menstrual cycle to alter the parasympathetic activity/sympathetic activity ratio in a manner that is effective to treat the subject for the condition. The subject methods find use in the treatment of a variety of different conditions, including various disease conditions, that increase in severity and/or occurrence during one or more phases of the menstrual cycle. Also provided are systems and kits for use in practicing the subject methods.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

As summarized above, the subject invention provides methods for treating a subject for a condition that has catamenial variations by modulating at least a portion of the autonomic nervous system during at least one predetermined phase of the menstrual cycle. The modulation may increase the parasympathetic activity/sympathetic activity ratio or decrease the parsympathetic activity/sympathetic activity ratio. In certain embodiments, the differential between the parasympathetic activity level and the sympathetic activity level will just be altered (increased or decreased), but the parasympathetic activity/sympathetic activity ratio may stay the same. In further describing the subject invention, representative embodiments of the subject methods are described first in greater detail, followed by a review of various representative applications in which the subject methods may find use. Next, a review of systems and kits for use in the subject methods is provided.

Methods

As noted above, the subject methods are methods for treating a female subject for a condition by modulating at least a portion of the autonomic nervous system during at least one predetermined phase of the subject's menstrual cycle. Conditions include those that are at least suspected of increasing in severity and/or occurrence during at least one phase of a subject's menstrual cycle and include known and to be discovered conditions that have catamenial variations. Accordingly, the subject methods may be employed to at least decrease the severity and/or occurrence of such a condition at least during the one or more phases of the menstrual cycle in which the condition is at least suspected of increasing in severity and/or occurrence.

The modulation of at least a portion of the autonomic nervous system during at least one predetermined menstrual cycle phase may be accomplished using any suitable method. For example, certain embodiments may include pharmacologically modulating and/or electrically modulating (i.e., applying electrical energy) at least a portion of the autonomic nervous system to modulate the parasympathetic activity/sympathetic activity ratio in a manner effective to treat a female for a condition, for example to increase the parasympathetic activity/sympathetic activity ratio or decrease the parsympathetic activity/sympathetic activity ratio. In certain embodiments the autonomic nervous system is modulated during at least one predetermined menstrual cycle phase to increase the sympathetic/parasympathetic ratio.

Exacerbation of certain medical conditions during specific phases of the menstrual cycle has long been recognized. Mechanisms of the cyclic variation are poorly understood, but are often attributed to fluctuation in reproductive hormones. However, the inventors of the subject invention have discovered that, in fact, variations in autonomic balance during the menstrual cycle, which may have evolved as adaptations for reproduction, may at least contribute partially if not completely, to catamenial variations in conditions and are independent of hormonal variations.

Accordingly, to address these autonomic system dependant-catamenial variations of conditions, embodiments of the subject invention include modulating at least a portion of a subject's autonomic nervous system during at least one predetermined phase of a subject's menstrual cycle to increase or decrease the parasympathetic activity/sympathetic activity ratio in a manner effective to treat the subject for the condition. In accordance with the subject invention, modulating at least a portion of autonomic nervous system may be achieved by any suitable method, e.g., administering an effective amount of at least one pharmacological agent and/or by applying stimulatory or inhibitory electrical energy, in a manner to effectively treat the subject for a condition.

Modulation of a subject's autonomic nervous system may include increasing one or more aspects of autonomic nervous system activity in at least a portion of the autonomic nervous system and/or decreasing one or more aspects of autonomic nervous system activity in at least a portion of the autonomic nervous system. By "modulating at least a portion of a subject's autonomic nervous system" and analogous terms is meant altering or changing at least a portion of a subject's autonomic nervous system by suitable means to provide a change, alteration or shift in at least one component or aspect of the autonomic nervous system to increase or decrease the parasympathetic activity/sympathetic activity ratio. The modulation of the autonomic nervous system may affect central motor output and/or nerve conduction and/or transmitter release and/or synaptic transmission and/or receptor activation, but in any event is a change that provides an increase or decrease in the parasympathetic activity/sympathetic activity ratio (as used herein "activity" and "function" are used interchangeably).

Embodiments of the subject methods may be employed to alter the dominance of the parasympathetic and sympathetic systems and/or may be employed to modulate the differential between the two systems. Modulation of the autonomic nervous system may be accomplished by increasing and/or decreasing activity in a portion of the autonomic nervous system. By "increasing activity" and analogous terms is meant the activity in at least a portion of the autonomic nervous system may be increased, relative to the activity level prior to employing the subject methods, to modulate at least a portion of the autonomic nervous system. For example, activity in any portion of the one or more nerve fibers of the parasympathetic nervous system and/or sympathetic nervous system may be increased or "up-regulated" to provide the desired ratio of parasympathetic activity/sympathetic activity. By "decreasing activity" and analogous terms is meant that activity in at least a portion of autonomic nervous system is decreased or inhibited, relative to its activity level prior to employing the subject methods, to modulate at least a portion of the autonomic nervous system. By "decreased" or "inhibited" activity (used herein interchangeably) is meant to include, but is not limited to, disruption, down-regulating, dampening and partial and complete blockage of function or nerve impulses in at least a portion of the autonomic nervous system. For example, activity in any portion of the one or more nerve fibers of the parasympathetic nervous system and/or sympathetic nervous system may be decreased or "down-regulated" to provide the desired ratio of parasympathetic activity/sympathetic activity.

Embodiments of the subject invention may include pharmacologically modulating at least a portion of a subject's autonomic nervous system to increase or decrease the parasympathetic activity/sympathetic activity ratio in at least a portion of the autonomic nervous system in a manner effective to treat a condition. Accordingly, embodiments of the subject invention may include pharmacologically increasing or decreasing parasympathetic activity in at least a portion of the autonomic nervous system and/or pharmacologically increasing or decreasing sympathetic activity in at least a portion of the autonomic nervous system. In other words, modulating at least a portion of autonomic nervous system to treat a condition may be achieved by administering an effective amount of at least one pharmacological agent, e.g., an amount sufficient to treat the condition of interest, during at least one predetermined phase of the menstrual cycle.

Embodiments of the subject invention may include electrically modulating at least a portion of a subject's autonomic nervous system to increase or decrease the parasympathetic activity/sympathetic activity ratio in at least a portion of the autonomic nervous system, in a manner effective to treat a condition, using electrical energy. Accordingly, embodiments of the subject invention may include electrically increasing or decreasing parasympathetic activity in at least a portion of the autonomic nervous system and/or electrically increasing or decreasing sympathetic activity in at least a portion of the autonomic nervous system. Embodiments may include electrically ablating one or more nerve fibers. In other words, modulating at least a portion of autonomic nervous system to treat a condition may be achieved by administering electrical energy to at least a portion of the autonomic nervous system in an amount sufficient to treat the condition of issue, during at least one phase of the menstrual cycle.

Accordingly, embodiments of the subject invention may include modulating at least a portion of a subject's autonomic nervous system to achieve a desired parasympathetic activity/sympathetic activity ratio, e.g., a ratio analogous to an average parasympathetic activity/sympathetic activity ratio observed in healthy females in the same or analogous menstrual cycle phase (e.g., of like age as the treated subject) not experiencing the condition being treated or not experiencing an exacerbation of the condition being treated. In other words, a parasympathetic activity/sympathetic activity ratio observed in a healthy, "like" or, i.e., analogous subject (e.g., a subject in the same or analogous phase of the menstrual cycle with respect to the exacerbation of the subject's condition and/or not experiencing an abnormality in the autonomic nervous system). As such, an average parasympathetic activity/sympathetic activity ratio as observed in healthy females may be referred to as an average "normal" ratio, whereas deviation from this average normal ratio to a degree that causes or at least exacerbates a condition may be referred to as an "abnormal" ratio (analogous descriptors may be used to refer to activity levels specific to the sympathetic nervous system and to the parasympathetic nervous system).

Embodiments of the subject invention may include modulating at least a portion of a subject's autonomic nervous system to achieve a desired parasympathetic activity/sympathetic activity ratio, wherein the desired ratio is one that is analogous to the average ratio observed in the same subject during a menstrual cycle phase that is different from the menstrual cycle phase during which the subject's autonomic nervous system is modulated (i.e., a phase other than the menstrual cycle phase in which the condition being treated is exacerbated). Accordingly, as the parasympathetic activity/sympathetic activity ratio varies during different phases of a female's menstrual cycle, a desired parasympathetic activity/sympathetic activity ratio may be one that is commensurate with that observed during a particular menstrual cycle phase or phases of the subject during which exacerbation of the condition of interest is not observed. For example, if exacerbation of a given condition is observed in the luteal phase and not in the follicular phase, a desired parasympathetic activity/sympathetic activity ratio may be one that is analogous to an average ratio observed during the follicular phase. In other embodiments, if exacerbation of the conditions is observed during the luteal phase of a subject, a desired parasympathetic activity/sympathetic activity ratio may be one that is analogous to an average ratio observed in females in the luteal phase, but who do not have the condition of interest or who have the condition of interest but the condition is not exacerbated in the luteal phase. In such instances, an average parasympathetic activity/sympathetic activity ratio observed in the same subject during a menstrual cycle phase other than the menstrual cycle phase during which modulation is performed (i.e., during which an exacerbation of a condition is observed) may be referred to as an average "normal" ratio, whereas deviation from this average normal ratio to a degree that causes or at least exacerbates a condition may be referred to as an "abnormal" ratio (analogous descriptors may be used to refer to activity levels specific to the sympathetic nervous system and to the parasympathetic nervous system).

Accordingly, a parasympathetic activity/sympathetic activity ratio observed in a subject during a predetermined menstrual cycle phase in which a condition is exacerbated may be characterized as abnormal with respect to (1) an average parasympathetic activity/sympathetic activity ratio observed in the same subject during a menstrual cycle phase other than the menstrual cycle phase during which the exacerbation of a condition is observed, and/or (2) an average parasympathetic activity/sympathetic activity ratio observed in a healthy, "like", i.e., analogous subject, in the same phase of the menstrual cycle as the phase in which the exacerbation of a condition is observed in the subject and/or (3) an average parasympathetic activity/sympathetic activity ratio observed in a healthy, "like", i.e., analogous subject, in a different phase of the menstrual cycle from the phase in which the exacerbation of a condition is observed in the subject.

For example, a subject may experience exacerbation of, e.g., an inflammatory condition or the like during the subject's luteal phase. Accordingly, referring to the embodiment described in (1) above, an average ratio of parasympathetic activity/sympathetic activity observed in the subject during, e.g., the follicular phase, may be characterized as normal wherein the deviation from this ratio as observed in the subject during the luteal phase may be characterized as abnormal. Referring to the embodiment described in (2) above, an average parasympathetic activity/sympathetic activity ratio observed in healthy analogous subjects during their luteal phases may be characterized as normal and the deviation from this ratio as observed in the subject experiencing the exacerbation of the condition during luteal phase may be characterized as abnormal. Referring to the embodiment described in (3) above, an average parasympathetic activity/sympathetic activity ratio observed in healthy analogous subjects during their follicular phases (for example) may be characterized as normal and the deviation from this ratio as observed in the subject experiencing the exacerbation of the condition during luteal phase may be characterized as abnormal. Such examples are for exemplary purposes only and in no way are intended to limit the scope of the invention.

The inventors of the subject invention have discovered that many conditions may be caused or at least exacerbated by a reproductive-facilitating shift of the autonomic nervous system during one or more phases of a female's menstrual cycle. For example, the inventors have discovered that a shift to a sympathetic bias (i.e., an shift to sympathetic dominance) during the luteal phase and/or early gestation may at least contribute to the exacerbation of certain conditions in many instances. While not being limited to any particular theory or hypothesis, in certain instances exacerbation of a condition may result from a shift to sympathetic bias during the luteal phase which promotes a transition to a more fertility-favorable immune and physiologic state of a female for accepting and nurturing a successful implantation. This shift to a sympathetic bias also promotes a shift to relative T helper (Th)-2 biased immunity which may favor maternal tolerance of an embryo by attenuating Th-1 mediated interference of implantation. Sympathetic bias may further support gestation through physiological effects such as increased cardiac output and systemic vascular resistance. In such instances where a shift to sympathetic bias has occurred, e.g., during the luteal phase and/or menses phase, and a condition is exacerbated, the autonomic nervous system may be modulated in accordance with the subject invention in a manner to achieve an increase in the parasympathetic activity/sympathetic activity ratio, e.g., to a parasympathetic activity/sympathetic activity ratio observed in one or more other phases of the subject's menstrual cycle or to a ratio analogous to one that has not shifted to sympathetic bias during the luteal phase. As a fertility-favorable sympathetic bias promotes a shift to T helper (Th)-2 bias, the level of Th2 in a subject may be determined and the result of that determination may be employed in the subject methods, e.g., to determine whether a fertility-favorable level of sympathetic activity is present in a subject (e.g. to determine whether to begin and/or continue and/or terminate modulation of the autonomic system). In sum, a parasympathetic activity/sympathetic activity ratio of a subject, e.g., analogous to a parasympathetic activity/sympathetic activity ratio observed during one or more particular phases of the menstrual cycle wherein exacerbation of a condition of interest is not observed, may be provided by the subject invention, e.g., by modulating at least a portion of the autonomic nervous system during (including just prior to the commencement of) one or more predetermined phases of the menstrual cycle wherein exacerbation of a condition of interest is observed.

A feature of embodiments of the subject methods is that the ratio of parasympathetic activity to sympathetic activity is increased. By "increased ratio of parasympathetic activity to sympathetic activity" and analogous terms is meant that this ratio (characterized by parasympathetic activity/sympathetic activity) is increased in at least a portion of the autonomic nervous system, where the increase is at least great enough to provide the desired results, e.g., great enough to treat a given condition.

While the ratio of parasympathetic function/sympathetic function may be increased according to embodiments of the subject invention, the net result may be a sympathetic bias (i.e., sympathetic dominance), parasympathetic bias (i.e., parasympathetic dominance) or the activities of the sympathetic system and parasympathetic system may be substantially equal (i.e., neither is dominant). By "bias" is meant that the particular "biased" component of the autonomic nervous system has a higher activity level than the other component. For example, a sympathetic bias refers to a higher level of sympathetic activity than parasympathetic activity, and vice versa, where such bias may be systemic or localized. The net result of the subject methods to treat a condition may be higher or greater parasympathetic activity relative to sympathetic activity in at least the area of the autonomic system targeted or rather in need of modulation, higher or greater sympathetic activity relative to parasympathetic activity in at least the area of the autonomic system targeted or rather in need of modulation, or substantially equal activity levels of parasympathetic activity and sympathetic activity.

A feature of embodiments of the subject methods is that the ratio of parasympathetic activity to sympathetic activity is decreased. By "decreased ratio of parasympathetic activity to sympathetic activity" and analogous terms is meant that this ratio (characterized by parasympathetic activity/sympathetic activity) is decreased in at least a portion of the autonomic nervous system, where the decrease is at least great enough to provide the desired results, e.g., great enough to treat a given condition.

While the ratio of parasympathetic function/sympathetic function may be decreased according to embodiments of the subject invention, the net result may be a sympathetic bias (i.e., sympathetic dominance), parasympathetic bias (i.e., parasympathetic dominance) or the activities of the sympathetic system and parasympathetic system may be substantially equal (i.e., neither is dominant).

As the subject methods include modulating at least a portion of a subject's autonomic nervous system, the modulation may be systemic or regional (i.e., localized). In other words, the entire autonomic nervous system may be modulated (e.g., the entire parasympathetic nervous system and/or sympathetic nervous system may be modulated) or only a portion of the autonomic nervous system may be modulated (e.g., only a portion of the parasympathetic nervous system and/or sympathetic nervous system may be modulated). Localization may be with respect to a particular area or even to a particular nerve fiber. Localization may be with respect to innervations of one or more particular organs.

Embodiments of the subject methods also include determining and/or monitoring one or more indicators, effects or results of the autonomic nervous system. For example, the level of T helper cells (Th1 and/or Th2) may be monitored, e.g., as an indicator of a parasympathetic activity/sympathetic activity ratio. Other indicators are described in greater detail below, and include, but are not limited to, heart rate variability ("HRV"), respiratory sinus arrhythmia, measures such a low frequency peak ("LF"), high frequency peak ("HF"), and LF/HF ratio, where such may be used as surrogates for autonomic balance. Any suitable indicator(s) may be monitored at any suitable time including before, during and after modulating the autonomic nervous system in accordance with the subject invention.

Methods of Treating a Subject for a Condition by Increasing or Decreasing the Parasympathetic Activity/Sympathetic Activity Ratio During at Least One Predetermined Phase of the Menstrual Cycle As indicated above, embodiments of the subject methods include treating a subject for a condition by modulating at least a portion of the autonomic nervous system during at least one predetermined phase of the subject's menstrual cycle to increase or decrease the parasympathetic activity/sympathetic activity ratio in a manner effective to treat the condition of interest. The subject methods may be employed to treat any condition at least suspected of being exacerbated during at least one phase of the subject's menstrual cycle. By "exacerbated" is meant broadly to include an increase in severity and/or occurrence of the condition.

Any area of the autonomic nervous system (any nerve of the autonomic nerve system) may be targeted according to the subject invention. Specific area(s) of the autonomic nervous system that may be modulated will vary, and include, but are not limited to, pre- and post ganglionic nerve fibers, ganglionic structures, efferent and afferent nerve fibers, the hypothalamus, receptors on the hypothalamus, afferent autonomic nerves (parasympathetic and sympathetic) and hormonal receptors on the hypothalamus. In certain embodiments, a given nerve fiber or the like may be modulated with respect to parasympathetic and/or sympathetic activity in more than one area of the nerve fiber.

The autonomic nervous system may be modulated using any suitable technique, including, but not limited to, surgical methods (e.g., surgical isolation of an effector structure from parasympathetic and/or sympathetic innervation, i.e., surgically isolating an effector structure from one or more parasympathetic and/or sympathetic nerve fibers associated with it); ablation (permanently or reversibly ablating a nerve by employing energy delivery devices or cryotherapy); cryoablation; thermoablation; microwave energy; focus ultrasound; magnetic fields including internal and external magnetic fields; laser energy; optical energy; radiofrequency energy; pacing mechanisms (e.g., implantable electrode-based pacing systems, external magnetic-based pacing system, and the like); transcutaneous electrical nerve stimulation ("TENS") or transmagentic stimulation ("TMS") (see for example George, M. Stimulating the Brain. Sci Amer 2003 September); pharmacological modulation; any suitable electrical modulation, and the like. Exemplary methods using pharmacological methods and electrical energy applying methods are now described in greater detail, where such descriptions are in no way intended to limit the scope of the invention as it is to be understood that modulation of the autonomic nervous system may be achieved using any suitable method.

Pharmacological Modulation of at Least a Portion of the Autonomic Nervous System As described above, embodiments include treating a subject for a condition by pharmacologically modulating at least a portion of the subject's autonomic nervous system during at least one predetermined menstrual phase to increase or decrease the parasympathetic activity/sympathetic activity ratio or increase parasympathetic activity relative to sympathetic activity. By "pharmacologically modulating at least a portion of a subject's autonomic nervous system" is meant altering or changing at least a portion of an autonomic nervous system by pharmacological means (i.e., administering a pharmaceutical agent to a subject) to provide a change, alteration or shift in at least one component or aspect of the autonomic nervous system. The pharmacological modulation of the autonomic nervous system may affect central motor output and/or nerve conduction and/or transmitter release and/or synaptic transmission and/or receptor activation, and the like, but in any event provides an increase (or decrease in certain embodiments) in the parasympathetic activity/sympathetic activity ratio during at least one predetermined menstrual phase.

For example, embodiments may include pharmacologically modulating at least a portion of a subject's autonomic nervous system to alter, shift or change the activity in at least one of the sympathetic system and parasympathetic system from a first state to a second state, where the second state is characterized at least by an increase in the parasympathetic activity/sympathetic activity ratio relative to the first state. One or more pharmacological agents may be employed to increase and/or decrease activity in at least a portion of the autonomic nervous system. For example, embodiments may include administering one or more pharmacological agents to achieve one or more of the following (but in any event to achieve a net result of an increase or decrease in parasympathetic activity/sympathetic activity ratio, relative to the parasympathetic activity/sympathetic activity ratio prior to pharmacological modulation): (1) increasing activity in at least one sympathetic nerve fiber to achieve an increase in activity at least a portion of the sympathetic system, (2) increasing activity in at least one parasympathetic nerve fiber to achieve an increase in activity in at least a portion of the parasympathetic system, (3) inhibiting activity in at least one sympathetic nerve fiber to achieve a decease in activity at least a portion of the sympathetic system, and (4) inhibiting activity in at least one parasympathetic nerve fiber to achieve a decease in activity in at least a portion of the parasympathetic system. Certain embodiments of the subject invention may include administering an effective amount of one or more pharmacological agents to both increase activity in at least a portion of the autonomic nervous system, e.g., increase activity in at least one parasympathetic nerve fiber, and inhibit activity in at least a portion of the autonomic nervous system, e.g., inhibit activity in at least one sympathetic nerve fiber, to treat condition.

Pharmacological modulation in accordance with the subject invention may be performed prior to and/or at the same time and/or subsequent to any other medical or clinical treatment regime such as any one or more of those described above, for example, electrical modulation of at least a portion of the subject's autonomic nervous system, e.g., as described in copending U.S. application Ser. No. 10/661,368, entitled "Treatment of Conditions Through Electrical Modulation of the Autonomic Nervous System", the disclosure of which is herein incorporated by reference, and the like. In other words, the subject methods may include other concomitant therapies or treatments to treat the same or different condition.

According to embodiments of the subject invention, pharmacological modulation is accomplished by at least administering an effective amount of at least one pharmacological agent to a subject to treat the subject for a condition caused, precipitated or otherwise exacerbated, influenced or affected during at least one predetermined menstrual phase, to increase the parasympathetic activity/sympathetic activity ratio during a given predetermined menstrual phase or phases. In other words, prior to practicing the subject invention, activity in at least a portion of the autonomic nervous system is at a level that is at least contributing to or otherwise affecting or exacerbating a condition such a disease condition, and as such modulation of the autonomic nervous system may be employed to treat the condition.

That is, embodiments of the subject methods include administering an effective amount, i.e., a therapeutically effective amount (also referred to as a pharmacologically effective amount), of one or more pharmacological agents to a subject to modulate at least a portion of the subject's autonomic nervous system. By "effective amount" and analogous terms is meant a dosage sufficient to modulate at least a portion of a subject's autonomic nervous system for a given period of time. The effective amount will vary with the age and physical condition of the subject, type and severity of the condition being treated, the duration of the treatment, the nature of any concurrent treatment, the pharmaceutically acceptable carrier used if any, and analogous factors within the knowledge and expertise of those skilled in the art. Introduction of an effective amount of a pharmacological agent to a subject resulting in a modulation of at least a portion of the autonomic nervous system that may be temporary or permanent.

In certain embodiments, more than one pharmacological agent may be administered at the same or different time as another pharmacological agent to treat a female for the same or different condition, where the pharmacological agents administered by differ in one or more respected, e.g., may be different types of agents or may be the same type pharmacological agent but that differ in mode of administration, dosage, etc.

The effective amount of a given pharmacological agent may vary somewhat from subject to subject, and may depend upon factors such as, but not limited to, the age of the subject, the health of the subject, the particular condition being treated, the form of the pharmacological agent, the route and method of delivery, etc., as noted above. Such dosages may be determined in accordance with routine pharmacological procedures known to those skilled in the art. Pharmacological agent and/or adjuvants may be administered to a subject in a single oral dose, one time a day or more for days, weeks, months, years, even as long as a subject's lifetime or as long as the subject experiences the condition of interest. For example, embodiment may include administering a given pharmacological agent one time a day over a prolonged period of time, e.g., over a particular time period coinciding with at least a portion of one or more menstrual cycle phases (e.g., over about the second half of the menstrual cycle, e.g., the luteal phase or at least the start of the luteal phase, the menses phase or at least the start of the menses phase, and the like), e.g., over about 1 week, e.g., over about 1-3 months, e.g., about 3 months to about 3 years or more, e.g., orally or with a medical infusion pump or similar device designed for delivery of a substance over a prolonged period.

The frequency of administration of a pharmacological agent may vary depending, e.g., on one or more of the factors described above. For example, the frequency of administration of a pharmacological agent may range from about 1 time per day to multiple times per day, e.g., about 2 times or more per day or as necessary to treat or otherwise control or manage a condition. The duration of therapy depends on the particular condition being treated and may range from as short as about 24 hours to as long as the life of the subject. For example, at least one autonomic nervous system modulating-pharmacological agent may be delivered to a subject during one or more predetermined phases of a subject's menstrual cycle such as during about the predetermined second half of the menstrual cycle, e.g., during a predetermined luteal phase or the like every month for months, years or even the entire lifetime of the subject. By "adjuvants" is meant a compound that, when used in combination with the one or more pharmacological agent compounds and/or compositions, augments or otherwise alters or modifies the resultant pharmacological and/or physiological responses.

Embodiments may include daily discrete or continuous unit doses wherein the total number of daily units may be equal to the total number of days of a given predetermined phase of the menstrual cycle, the total number of days of a month or menstrual cycle, and the like, in the form of a pack. For example, embodiments may include daily discrete or continuous unit doses wherein the total number of daily units may be equal to the total number of days of a month or menstrual cycle, e.g., in the form of a monthly pack. Such a monthly pack may include a plurality of unit dosage forms having the same or different dosages of a pharmacological agent. For example, embodiments may include a monthly pharmacological agent pack wherein the dosage of active agent of certain unit dosage forms of the pack to be administered to a subject during one or more predetermined phases of the menstrual cycle (e.g., one or more predetermined phases of the menstrual cycle wherein exacerbation of a condition is observed, e.g., the second half of the menstrual cycle, e.g., the luteal phase and/or menses phase) may differ in dosage from one or more other unit dosage forms to be administered to the subject during one or more other predetermined phases of the menstrual cycle (e.g., one or more other predetermined phases of the menstrual cycle wherein exacerbation of a condition is not observed).

Depending on the particular pharmacological agent administered to a subject, the pharmacological agent may be administered to a subject using any convenient means capable of resulting in the desired modulation of the autonomic nervous system. Thus, the at least one pharmacological agent may be incorporated into a variety of formulations for therapeutic administration. More particularly, the pharmacological agent may be formulated into pharmaceutical compositions by combination with appropriate, pharmaceutically acceptable carriers. By "pharmaceutically acceptable carrier" is meant a component such as a carrier, diluent, excipient, and the like of a composition that is compatible with the particular pharmacological agent and other optional ingredients of the subject pharmacological agent compositions in that a pharmaceutically acceptable carrier may be combined with the pharmacological agent without eliminating the biological or therapeutically effective activity of the pharmacological agent, and is suitable for use in subjects as provided herein without undue adverse side effects (such as toxicity, irritation, allergic response, and death). Side effects are "undue" when their risk outweighs the benefit provided by the pharmacological agent. Non-limiting examples of pharmaceutically acceptable components include, but are not limited to, any of the standard pharmaceutical carriers such as phosphate buffered saline solutions, water, emulsions such as oil/water emulsions or water/oil emulsions, microemulsions, and various types of wetting agents. Accordingly, the pharmacological agent employed in the subject methods may be formulated into preparations in solid, semi-solid (e.g., gel), liquid or gaseous forms, such as tablets, capsules, powders, granules, ointments, solutions, suppositories, injections, inhalants and aerosols. As such, administration of a pharmacological agent may be achieved in various ways, including, but not limited to, oral, buccal (e.g. sub-lingual), rectal, topical (including both skin and mucosal surfaces, including airway surfaces), parenteral (e.g., subcutaneous, intramuscular, intradermal, intravenous and intrathecal), intraperiactivityal, transdermal, intracheal, intravaginal, endocervical, intrathecal, intranasal, intravesicular, in or on the eye, in the ear canal, etc., administration. In certain embodiments, a given pharmacological agent may be administered via a transdermal patch or film system such as or analogous to that described, e.g., in U.S. Pat. Nos. 6,503,532; 5,302,395; 5,262,165; 5,248,501; 5,232, 702; 5,230,896; 5,227,169; 5,212,199; 5,202,125; 5,173,302; 5,154,922; 5,139,786; 5,122,383; 5,023,252; 4,978,532; 5,324,521; 5,306,503; 5,302,395; 5,296,230; 5,286,491; 5,252,334; 5,248,501; 5,230,896; 5,227,169; 5,212,199; 5,202,125; 5,173,302; 5,171,576; 5,139,786; 5,133,972; 5,122,383; 5,120,546; 5,118,509; 5,077,054; 5,066,494; 5,049,387; 5,028,435; 5,023,252; 5,000,956; 4,911,916; 4,898,734; 4,883,669; 4,882,377; 4,840,796; 4,818,540; 4,814,173; 4,806,341; 4,789,547; 4,786,277; 4,702,732; 4,690,683; 4,627,429; and 4,585,452, the disclosures of which are herein incorporated by reference.

As noted above, embodiments may include pharmaceutical formulations for oral administration that may be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc., suitable for ingestion by the patient. Pharmaceutical preparations for oral use may be obtained through combination of at least one pharmacological agent with a solid excipient, optionally grinding a resulting mixture, and processing the mixture of granules, after adding suitable additional compounds, if desired, to obtain tablets or dragee cores. Suitable solid excipients include, but are not limited to, carbohydrate or protein fillers and include, but are not limited to sugars, including lactose, sucrose, mannitol, or sorbitol; starch from corn, wheat, rice, potato, or other plants; cellulose such as methyl cellulose, hydroxypropylmethyl-cellulose or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate; with optional lubricants, such as talc or magnesium stearate; and if desired, with diluents, buffering agents, moistening agents, preservatives and flavoring agents.

Accordingly, pharmacological formulations suitable for oral administration in accordance with the subject invention may be present in discrete units, such as capsules, cachets, lozenges, tablets, and the like, each containing a predetermined amount of the active pharmacological agent; as a powder or granules; as a solution or a suspension in an pharmacological formulations may be prepared by any suitable method of pharmacy which includes, but is not limited to, bringing into association the active pharmacological agent and a suitable carrier (which may contain one or more optional ingredients as noted above). For example, pharmacological formulations for use with the subject invention may be prepared by uniformly and intimately admixing the active pharmacological agent with a liquid or finely divided solid carrier, or both, and then, if necessary, shaping the resulting mixture. For example, a tablet may be prepared by compressing or molding a powder or granules containing the active pharmacological agent, optionally with one or more accessory ingredients. Compressed tablets may be prepared by compressing, in a suitable machine, the pharmacological agent in a free-flowing form, such as a powder or granules optionally mixed with a binder, lubricant, inert diluent, and/or surface active/dispersing agent(s). Molded tablets may be made by molding, in a suitable machine, the powdered pharmacological agent moistened with an inert liquid binder.

A pharmacological agent of this invention may also be administered in the form of suppositories for rectal administration of the drug. These formulations may be prepared by mixing a pharmacological agent with a suitable non-irritating vehicle or excipient which is solid at ordinary temperatures but liquid at the rectal temperatures and will therefore melt in the rectum to release the drug. Such materials include, but are not limited to, cocoa butter, carbowaxes and polyethylene glycols. Embodiments include a pharmacological agent made into suppositories by mixing with a variety of bases such as emulsifying bases or water-soluble bases.

A pharmacological agent of this invention may also be administered by intranasal, intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995).

For example, embodiments may also include a pharmacological agent in an aerosolized, atomized or nebulized vapor form, e.g., administrable via a metered dose device or nebulizer, and the like such that embodiments also include aerosolizing, vaporing or nebulizing one or more pharmacological agents for administration to a subject. Accordingly, a pharmacological agent may be utilized in aerosol formulation or an analogous formulation to be administered via inhalation or analogous means. The pharmacological agent employed in the practice of the present invention may be formulated into pressurized acceptable propellants such as dichlorodifluoromethane, propane, nitrogen and the like.

A pharmacological agent employed in the subject invention may be delivered transdermally, by a topical route, formulated as applicator sticks, solutions, suspensions, emulsions, gels, creams, ointments, pastes, jellies, paints, powders, and aerosols. For example, embodiments may include a pharmacological agent in the form of a discrete patch or film or plaster or the like adapted to remain in intimate contact with the epidermis of the recipient for a period of time. For example, such transdermal patches may include a base or matrix layer, e.g., polymeric layer, in which one or more pharmacological agents are retained. The base or matrix layer may be operatively associated with a support or backing. Pharmacological formulations suitable for transdermal administration may also be delivered by iontophoresis and may take the form of an optionally buffered aqueous solution of the pharmacological compound. Suitable formulations may include citrate or bis/tris buffer (pH 6) or ethanol/water and contain a suitable amount of active ingredient.

A pharmacological agent of the invention may also be delivered as microspheres for slow release in the body. For example, microspheres may be administered via intradermal injection of drug-containing microspheres, which slowly release subcutaneously (see Rao, *J. Biomater Sci. Polym. Ed.* 7:623-645, 1995); as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

A pharmaceutical formulation of the invention may be provided as a salt and may be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, a preparation may be a lyophilized powder that is combined with buffer prior to use.

Pharmacological formulations of the subject invention may be useful for parenteral administration, such as intravenous ("IV") administration, intramuscular ("IM"), subcutaneous ("SC" or "SQ"), mucosal. The formulations for administration may include a solution of the pharmacological agent dissolved in a pharmaceutically acceptable carrier. Among the acceptable vehicles and solvents that may be employed, include, but are not limited to, water and Ringer's solution, an isotonic sodium chloride, etc. In addition, sterile fixed oils may conventionally be employed as a solvent or suspending medium. For this purpose any bland fixed oil may be employed including synthetic mono- or diglycerides. In addition, fatty acids such as oleic acid can likewise be used in the preparation of injectables. Accordingly, a pharmacological agent may be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of pharmacological agent in these formulations may vary widely, and will be selected based on fluid volumes, viscosities, body weight, and the like, in accordance with the particular mode of administration selected and the patient's needs. For IV administration, the formulation may be a sterile injectable preparation, such as a sterile injectable aqueous or oleaginous suspension. This suspension may be formulated according to the known art using those suitable dispersing or wetting agents and suspending agents. The sterile injectable preparation may also be a sterile injectable solution or suspension in a nontoxic parenterally-acceptable diluent or solvent, such as a solution of 1,3-butanediol, and the like. Accordingly, pharmacological formulations suitable for parenteral administration may include sterile aqueous and non-aqueous injection solutions of one or more active pharmacological agents, which preparations may be isotonic with the blood of the intended recipient. These preparations may contain, buffers and solutes which render the formulation isotonic with the blood of the intended recipient. Aqueous and non-aqueous sterile suspensions may include suspending agents and thickening agents. The formulations may be presented in single- or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind described above.

In other embodiments, the pharmacological formulations of the invention may be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the pharmacological agent into the target cells in vivo. (See, e.g., Al-Muhammed, *J. Microencapsul.* 13:293-306, 1996; Chonn, *Curr. Opin. Biotechnol.* 6:698-708, 1995;

Ostro, *Am. J. Hosp. Pharm.* 46:1576-1587, 1989). Accordingly, embodiments may include a pharmacological agent administered as liposomal formulations of the pharmacological agent. Methods for preparing liposomal suspensions are known in the art and thus will not be described herein in great detail. Briefly, in those embodiments where the pharmacological agent is an aqueous-soluble pharmacological agent, the pharmacological agent may be incorporated into lipid vesicles using conventional liposome technology. In such instances, due to the water solubility of the pharmacological agent, the pharmacological agent may be substantially entrained within the hydrophilic center or core of the liposomes. The lipid layer employed may be of any conventional composition and may either contain cholesterol or may be cholesterol-free. When the pharmacological agent of interest is water-insoluble, the pharmacological agent may be substantially entrained within the hydrophobic lipid bilayer which forms the structure of the liposome employing conventional liposome formation technology. In either instance, the liposomes which may be produced may be reduced in size, as through the use of standard sonication and homogenization techniques. Embodiments of liposomal formulations containing the pharmacological agent of interest may be lyophilized to produce a lyophilizate which may be reconstituted with a pharmaceutically acceptable carrier, such as water, to regenerate a liposomal suspension.

Embodiments of the pharmacological agent employed in the practice of the subject invention may include pharmaceutical compositions that may be prepared from water-insoluble compounds, or salts thereof, such as aqueous base emulsions. In such embodiments, the pharmacological composition will typically contain a sufficient amount of pharmaceutically acceptable emulsifying agent to emulsify the desired amount of the pharmacological agent. Useful emulsifying agents include, but are not limited to, phosphatidyl cholines, lecithin, and the like.

As noted above, in addition to active pharmacological agent, the pharmaceutical compositions of the subject invention may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Furthermore, pharmacological compositions may, though not always, contain microbial preservatives. Microbial preservatives that may be employed include, but are not limited to, methylparaben, propylparaben, and benzyl alcohol. The microbial preservative may be employed when the pharmacological formulation is placed in a vial designed for multidose use. Pharmaceutical compositions for use in practicing the subject methods may be lyophilized using techniques well known in the art.

Pharmaceutically acceptable excipients, such as vehicles, adjuvants, carriers or diluents, that may be employed in the subject invention are readily available to the public. Moreover, pharmaceutically acceptable auxiliary substances, such as pH adjusting and buffering agents, tonicity adjusting agents, stabilizers, wetting agents and the like, are readily available to the public.

Embodiments may also include administration of a pharmacological agent using a pharmacological delivery device such as, but not limited to, pumps (implantable or external devices and combinations of both (e.g., certain components may be implantable and others may be external to the body such as controls for the implantable components), epidural injectors, syringes or other injection apparatus, catheter and/or reservoir operatively associated with a catheter, etc. For example, in certain embodiments a delivery device employed to deliver a given pharmacological agent to a subject may be a pump, syringe, catheter or reservoir operably associated with a connecting device such as a catheter, tubing, or the like. Containers suitable for delivery of a pharmacological agent to a pharmacological agent administration device include instruments of containment that may be used to deliver, place, attach, and/or insert the pharmacological agent into the delivery device for administration of the pharmacological agent to a subject and include, but are not limited to, vials, ampules, tubes, capsules, bottles, syringes and bags. Embodiments may also include administration of a pharmacological agent via a biodegradable implant drug delivery device. Such may be accomplished by employing syringes to deposit such a biodegradable delivery device under the skin of a subject. The implants degrade completely, so that removal is not necessary.

Embodiments may include employing an electrode to deliver a pharmacological agent to a subject. For example, an electrode may be used that has a small port at its tip which is connected to a reservoir or pump containing a pharmacological agent. The pharmacological agent delivery electrode may be implanted using any suitable technique such as surgical cut down, laproscopy, endoscopy, percutaneous procedure, and the like. In certain embodiments a reservoir or pump may also be implanted in the subject's body. The pharmacological agent delivery electrode, or other analogous device, may be controllable such that the amount of pharmacological agent delivered, the rate at which the pharmacological agent may be delivered, and the time period over which the pharmacological agent may be delivered, etc., may be controllable and may be adjusted.

In certain embodiments, the pharmaceutically acceptable carrier may be preservative free. By "preservative free" is meant the substantial absence of chemical, antibacterial, antimicrobial, or antioxidative additives, or the like, from the pharmaceutically acceptable carriers of the present invention. "Substantial absence" may mean that no preservative is present in the compositions or that trace amounts may be present that impart no detectable effect otherwise attributable to a preservative. For example, the pharmaceutically acceptable carrier may be characterized by the substantial absence of chemical, antibacterial, antimicrobial, or antioxidative additives or the like (e.g., contain less than about 5.0, 4.0, 3.0, 2.0, 1.0, 0.5, 0.1, 0.05, 0.01, or even about 0.00 percent by weight of a preservative). Further, such formulations may be substantially or essentially free of alcohols such as ethanol (e.g., contain less than about 5.0, 4.0, 3.0, 2.0, 1.0, 0.5, 0.1, 0.05, 0.01, or even about 0.00 percent by weight of alcohols such as ethanol). Examples of suitable pharmacological formulations include, but are not limited to, formulations that include one or more active pharmacological agents and physiological saline solution (optionally including other typical ingredients such as other active agents and buffers).

As noted above, in pharmaceutical dosage forms, a given pharmacological agent may be administered alone or in appropriate association with, as well as in combination with, other pharmaceutically active compounds. As used herein, "administered with" means that a given pharmacological agent and at least one other adjuvant (including one or more other different pharmacological agents) are administered at times sufficiently close that the results observed are indistinguishable from those achieved when the pharmacological agent and at least one other adjuvant are administered at the same point in time. The pharmacological agent and at least one other adjuvant may be administered simultaneously (i.e., concurrently) or sequentially. Simultaneous administration may be carried out by mixing a given pharmacological agent and at least one other adjuvant prior to administration, or by administering a given pharmacological agent and at least one other adjuvant at the same point in time. Such administration may be at different anatomic sites or using different routes of administration. The phrases "concurrent administration," "administration in combination," "simultaneous administration" or "administered simultaneously" may also be used interchangeably and mean that a given pharmacological agent and at least one other adjuvant are administered at the same point in time or immediately following one another. In the latter case, the pharmacological agent and at least one other adjuvant are administered at times sufficiently close that the results produced are synergistic and/or are indistinguishable from those achieved when the at least one pharmacological agent and at least one other adjuvant are administered at the same point in time. Alternatively, a pharmacological agent may be administered separately from the administration of an adjuvant, which may result in a synergistic effect or a separate effect. The methods and excipients described herein are merely exemplary and are in no way limiting.

Unit dosage forms for oral or rectal administration such as syrups, elixirs, and suspensions may be provided wherein each dosage unit, for example, teaspoonful, tablespoonful, tablet or suppository, contains a predetermined amount of a pharmacological agent. Similarly, unit dosage forms for injection or intravenous or other suitable administration route may include the pharmacological agent(s) in a composition as a solution in sterile water, normal saline or another pharmaceutically acceptable carrier.

The term "unit dosage form," and analogous terms as used herein refers to physically discrete units suitable as unitary dosages for human and animal subjects, each unit containing a predetermined quantity of pharmacological agent(s) calculated in an amount sufficient to produce the desired effect in association with a pharmaceutically acceptable diluent, carrier or vehicle. The specifications for the unit dosage forms of a given pharmacological agent employed in the practice of the present invention depend on, for example, the particular pharmacological agent employed and the effect to be achieved, the pharmacodynamics associated with the particular pharmacological agent in the subject, etc.

As noted above, those of skill in the art will readily appreciate that dose levels may vary as a function of the specific pharmacological agent, the nature of the delivery vehicle, and the like. Dosages for a given pharmacological agent are readily determinable by those of skill in the art by a variety of means. Exemplary dosage levels are provided herein and are not to be construed to limit the scope of the invention in any manner.

A wide variety of different pharmacological agents may be employed in the practice of the subject methods, where the particular pharmacological agent or combination of pharmacological agents employed will depend on, e.g., the subject being treated, the condition being treated, duration of treatment, whether it is desired to increase activity in the parasympathetic system and/or increase activity in the sympathetic system and/or decrease activity in the sympathetic system and/or decrease activity in the parasympathetic system, etc.

As noted above, certain embodiments include pharmacologically modulating at least a portion of the autonomic nervous system during at least one predetermined menstrual cycle phase of the subject to increase the parasympathetic activity/sympathetic activity ratio. Such may be the case, for example, wherein the subject methods are employed to treat conditions such as, but not limited to: cardiovascular conditions, neurodegenerative conditions, orthopedic inflammatory conditions, inflammatory conditions, lymphoproliferative conditions, autoimmune conditions, inflammatory conditions, infectious diseases, pulmonary conditions, gastrointestinal conditions, endocrine conditions, genitourinary conditions, skin conditions, aging associated conditions, Th-2 dominant conditions, conditions that cause hypoxia; conditions that cause hypercarbia; conditions that cause hypercapnia; conditions that cause acidosis; conditions that cause acidemia; neurologic conditions, OB-GYN conditions; sudden death syndromes; menstrual related disorders; peripartum and pregnancy related disorders; fibrosis; post-operative recovery conditions; post-procedural recovery conditions; chronic pain; trauma; bacterial infections; and fibromyalgia. Representative pharmacological agents (and analogs, derivatives and salts thereof) that may be used in this regard include, but are not limited to, one of more of the following:

beta-blockers (e.g., atenolol (e.g., as sold under the brand names TENORMIN), betaxolol (e.g., as sold under the brand name KERLONE), bisoprolol (e.g., as sold under the brand name ZEBETA), carvedilol (e.g., as sold under the brand name COREG), esmolol (e.g., as sold under the brand name BREVIBLOC), labetalol (e.g., as sold under the brand name NORMODYNE), metoprolol (e.g., as sold under the brand name LOPRESSOR), nadolol (e.g., as sold under the brand name CORGARD), pindolol (e.g., as sold under the brand name VISKEN), propranolol (e.g., as sold under the brand name INDERAL), sotalol (e.g., as sold under the brand name BETAPACE), timolol (e.g., as sold under the brand name BLOCADREN), carvedilol, and the like);

aldosterone antagonists (e.g., spironolactone, eplerenone, and the like);

angiotensin II receptor blockades (e.g., candeartan (e.g., available under the brand name ALTACAND), eprosarten mesylate (e.g., available under the brand name TEVETAN), irbesartan (e.g., available under the brand name AVAPRO), losartan (e.g., available under the brand name COZAAR), etelmisartin (e.g., available under the brand name MICARDIS), valsartan (e.g., available under the brand name DIOVAN), and the like);

angiotensin converting enzyme ("ACE") inhibitors (e.g., benazapril (e.g., available under the brand name LOTENSIN), captopril (e.g., available under the brand name CAPOTEN) enalapril (e.g., available under the brand name VASOTEC) fosinopril (e.g., available under the brand name MONOPRIL) lisinopril (e.g., available under the brand name PRINIVIL) moexipril (e.g., available under the brand name UNIVASC) quinapril (e.g., available under the brand name ACCUPRIL) ramipril (e.g., available under the brand name ALTACE) trandolapril (e.g., available under the brand name MAVIK), and the like);

statins (e.g., atorvastatin (e.g., available under the brand name LIPITOR), cerivastatin (e.g., available under the brand name BAYCOL), fluvastatin (e.g., available under the brand name LLESCOL), lovastatin (e.g., available under the brand name MEVACOR), prevastatin (e.g., available under the brand name PRAVACHOL), simvastatin (e.g., available under the brand name ZOCOR), and the like);

triglycerides lowering agents (e.g., fenofibrate (e.g., available under the brand name TRICOR), genfibrozil (e.g., available under the brand name LOPID), and the like);

niacin;

diabetes agents (e.g., acarbose (e.g., available under the brand name PRECOSE), glimepiride (e.g., available under the brand name AMARYL), glyburide (e.g., available under the brand names MICRONASE, DIABETA), metformin (e.g., available under the brand name GLUCOPHASGE), miglitol (e.g., available under the brand name GLYCET), pioglitazone (e.g., available under the brand name ACTOS), repaglinide (e.g., available under the brand name PRANDIN), rosiglitazone (e.g., available under the brand name AVANDIA), and the like);

immunomodulators (e.g., interferon beta-1B (e.g., available under the brand name BETASERON), interferon alfa-2A (e.g., available under the brand name ROFERON-A) interferon alfa-2B (e.g., available under the brand name INTRON-A), interferon alfa-2B and Ribavirin combo pack (e.g., available under the brand name REBETRON), interferon alfa-N3 (e.g., available under the brand name ALFERON N), interferon beta-1A (e.g., available under the brand name AVONEX), interferon beta-1B, interferon gamma immunoregulatory antibodies that bind to or react with one of the following antigens: CD4, gp39, B7, CD19, CD20, CD22, CD401, CD40, CD40L and CD23, rituximab (e.g., available under the brand name RITUXAN), any chemical or radiopharmaceutical linked or conjugated antibodies that bind to or react with one of the following antigens: CD4, gp39, B7, CD19, CD20, CD22, CD401, CD40, CD40L and CD23), and the like);

nicotine;

sympathomimetics (e.g., trimethaphan, clondine, reserpine, guanethidine, and the like);

antihistamines (e.g., available under the brand name BENADRYL, diphenhydramine, available under the brand name ACTIFED, and the like);

cholinergics (e.g., bethanechol, oxotremorine, methacoline, cevimeline, and the like);

acetylcholinesterase inhibitors (e.g., edrophonium, neostigmine, donepezil, tacrine, echothiophate, diisopropylfluorophosphate, demecarium, pralidoxime, galanthamine, tetraethyl pyrophosphate, parathoin, malathion, isoflurophate, metrifonate, physostigmine, rivastigmine, abenonium acetylchol, carbaryl acetylchol, propoxur acetylchol, aldicarb acetylchol, and the like);

magnesium and magnesium sulfates;

calcium channel blockers (e.g., amlodipine besylate (e.g., available under the brand name NORVASC), diltiazem hydrochloride (e.g., available under the brand names. CARDIZEM CD, CARDIZEM SR, DILACOR XR, TIAZAC), felodipine plendil isradipine (e.g., available under the brand names DYNACIRC, DYNACIRC CR), nicardipine (e.g., available under the brand name CARDENE SR), nifedipine (e.g., available under the brand names ADALAT CC, PROCARDIA XL), nisoldipine sulfur (e.g., available under the brand name SULAR), verapamil hydrochloride (e.g., available under the brand names CALAN SR, COVERA HS, ISOPTIN SR, VERELAN) and the like);

muscarinics (e.g., muscarine, pilocarpine, and the like);

sodium channel blockers, (e.g., moricizine, propafenone, encainide, flecainide, tocainide, mexiletine, phenytoin, lidocaine, disopyramide, quinidine, procainamide, and the like);

glucocorticoid receptor blockers (e.g., mifepristone, and the like);

peripheral andrenergic inhibitors (e.g., guanadrel (e.g., available under the brand name HYLOREL), guanethidine monosulfate (e.g., available under the brand name ISMELIN), reserpine (e.g., available under the brand names SERPASIL, MECAMYLAMINE, HEXEMETHONIUM), and the like);

blood vessel dilators (e.g., hydralazine hydrocholoride (e.g., available under the brand name APRESOLINE), minoxidil (e.g., e.g., available under the brand name LONITEN), and the like);

central agonists (e.g., alpha methyldopa (e.g., available under the brand name ALDOMET), clonidine hydrochloride (e.g., available under the brand name CATAPRES), guanabenz acetate (e.g., available under the brand name WYTENSIN), guanfacine hydrochloride (e.g., available under the brand name TENEX), and the like;

combined alpha and beta-blockers (e.g., carvedilol (e.g., available under the brand name COREG), labetolol hydrochloride (e.g., available under the brand names NORMODYNE, TRANDATE), and the like);

alpha blockers (e.g., doxazosin mesylate (e.g., available under the brand name CARDURA), prazosin hydrochloride (e.g., available under the brand name MINIPRESS), terazosin hydrochloride (e.g., available under the brand name HYTRIN), and the like);

combination diuretics (e.g., amiloride hydrochloride+hydrochlorothiazide (e.g., available under the brand name MODURETIC), spironolactone+hydrochlorothiazide (e.g., Aldactazide), triamterene+hydrochlorothiazide (e.g., available under the brand names DYAZIDE, MAXZIDE) and the like); potassium sparing diuretics (e.g., amiloride hydrochloride (e.g., available under the brand name MIDAMAR), spironolactone (e.g., available under the brand name ALDACTONE), triamterene (e.g., available under the brand name DYRENIUM), and the like); nitrates (e.g., L-arginine, (e.g., available under the brand names NITROGLYCERIN DEPONIT, MINITRAN, NITROPAR, NITROCINE, NITRO-DERM, NITRO DISC, NITRO-DUR, NITROGARD, NITROGLYCERIN, NITROGLYCERIN T/R, NITRO-TIME, NITROL OINTMENT, NITROLINGUAL SPRAY, NITRONG, NITRO-BID, NITROPRESS, NITROPREX, NITRO S.A., NITROSPAN, NITROSTAT, NITROTRANS SYSTEM, NITRO-TRANSDERMAL, NITROTIME, TRANSDERM-NITRO, TRIDIL. PENTAERYTHRITOL TETRANITRATE PERITRATE, PERITRATE S.A. ERYTHRITYL TETRANITRATE CARDILATE ISOSORBIDE DINITRATE/PHENOBARBITAL ISORDIL W/PB ISOSORBIDE MONONITRATE IMDUR, ISMO, ISOSORBIDE MONONITRATE, MONOKET ISOSORBIDE NITRATE DILATRATE-SR, ISO-BID, ISORDIL, ISORDIL TEMBIDS, ISORDIL DINITRATE, ISORDIL DINITRATE LA, SORBITRATE, SORBITRATE SA), and the like);

cyclic nucleotide monophosphodiesterase ("PDE") inhibitors (e.g., vardenafil (e.g., available under the brand name LEVITRA), sildenafil (e.g., available under the brand name VIAGRA) tadalafil (e.g., available under the brand name CIALIS) and the like);

alcohols;

vasopressin inhibitors (e.g., atosiban (Tractocile), AVP VIa (OPC-21268, SR49059 (Relcovaptan)), V2 (OPC-31260, OPC-41061 (Tolvaptan), VPA-985 (Lixivaptan), SR121463, VP-343, FR-161282) and mixed V1a/V2 (YM-087 (Conivaptan), JTV-605, CL-385004) receptor antagonists, and the like);

oxytocin inhibitors (e.g., terbutaline, ritodrine, and the like);

glucagons like peptide 1;

relaxin hormone;

renin inhibitors (e.g., Aliskiren, and the like);

estrogen and estrogen analogues (e.g., estradiols, and the like) and metabolites;

progesterone inhibitors;

testosterone inhibitors;

gonadotropin-releasing hormone analogues (GnRH—As);

gonadotropin-releasing hormone inhibitors (e.g., Leuprolide Acetate, and the like);

vesicular monoamine transport (VMAT) inhibitors (e.g., tetrabenazine, and the like); dipeptidyl peptidase (DP) IV inhibitors (DP4 inhibitors) (e.g., LAF237, P93/01, P32/98, valine pyrrolidide, and the like);

melatonin; and the like;

anti-coagulants (e.g., ximelagatran (EXANTA); hirulog (BIVALIRIDIN); abciximab (REOPRO); dipridamole (AGGRENOX); anagrlide (AGRILYN); clopiogrel (PLAVIX); dipridamole (PERSANTINE); eptifabatide (INTEGRILIN); ticlopidine (TICLID); tirofibam (AGGRASTAT); ardeparin (NORMIFLO); dalteparin (FRAGMIN); dnaparoid (ORGARIN); enoxaparin (LOVENOX); lepiudin (REFLUDAN); heparin; warfarin; alteplase (ACTIVASE), t-PA); reteplase (RETEVASE); streptokinase; urokinase; aminocaproic acid (AMICAR); cilostazol (PLETAL); pentoxifylline (TRENTAL); and the like).

As noted above, one or more of the above-described a pharmacological agents may be employed in the practice of the subject methods and may be of particular use in modulating at least a portion of a subject's autonomic nervous system to increase the parasympathetic activity/sympathetic activity ratio. However, the subject methods are not limited to the above-described active agents as other pharmacological agents may be employed in the practice of the subject methods. For example, the below-described pharmacological agents may be employed in the practice of the subject methods, where one or more of the following pharmacological agents may be of particular use in modulating at least a portion of a subject's autonomic nervous system to decrease the parasympathetic activity/sympathetic activity ratio. Such may be the case, for example, wherein the subject methods are employed to treat certain bacterial infections, e.g., bacterial vaginosis, etc. Other conditions that may be treated by decreasing the parasympathetic activity/sympathetic activity ratio include, but are not limited to: infertility, early pregnancy loss, spontaneous abortion, subfertility, failure of implantation, amenorrhea, luteal insufficiency, dysmenorrhea, pelvic pain, depression, bipolar disorder, bacterial vaginosis, obesity, multiple sclerosis, and the like.

Representative pharmacological agents (and analogs, derivatives and salts thereof) that may be employed in the practice of the subject methods (e.g., to modulating at least a portion of a subject's autonomic nervous system during at least one predetermined menstrual cycle phase of the subject to increase the sympathetic activity/parasympathetic activity ratio) include, but are not limited to, one or more of the following:

beta agonists (e.g., dobutamine, metaproterenol, terbutaline, ritodrine, albuterol, and the like);

alpha agonists (e.g., selective alpha 1-adrenergic blocking agents such as phenylephrine, metaraminol, methoxamine; prednisone and steroids and the like, (e.g., available under the brand names CORATN, DELTASONE, LIQUID PRED, MEDICORTEN, ORASONE, PANASOL-S, PREDNICEN-M, PREDNISONE INTENSOL));

indirect agents that include norepinephrine (e.g., ephedrine, ampthetamines, phenylpropanolamines, cyclopentamines, tuaminoheptanes, naphazolines, tetrahydrozolines, and the like);

epinephrine and the like;
norepinephrine and the like;
acetylcholine and the like;
sodium and the like;
calcium and the like;
angiotensin I and the like;
angiotensin II and the like;
angiotensin converting enzyme I ("ACE I") and the like;
angiotensin converting enzyme II ("ACE II") and the like;
aldosterone and the like;
potassium channel blockers and magnesium channel blockers (e.g., valproate (sodium valproate, valproic acid), lithium, and the like);
cocaine and the like;
amphetamines and the like;
ephedrine and the like;
terbutaline and the like;
dopamine and the like;
doputamine and the like;
antidiuretic hormone ("ADH") (also known as vasopressin) and the like;
oxytocin (including PITOCINE) and the like; and
THC cannabinoids.

As noted above, a combination of two or more of any of the above noted agents or like agents may be employed.

As noted above, certain embodiments may include administering a pharmacologically effective amount of a first pharmacological agent and a pharmacologically effective amount of at least a second, different pharmacological agent, e.g., concurrently administered, where the two may differ in one or more of a variety of aspects, e.g., dosage, type, route of administration, etc. For example, embodiments may include administering a first type of pharmacological agent and at least one other type of pharmacological agent to provide an enhanced therapeutic effect. By "enhanced therapeutic effect" is meant that at least the initial relief of the particular condition being treated by the first pharmacological agent employed occurs more quickly with a combination of the first pharmacological agent and at least one other different pharmacological agent, as compared to the same doses of each component given alone, or that doses of one or all component(s) are below what would otherwise be a minimum effective dose (a "sub-MED").

Accordingly, embodiments of the subject invention includes treating a subject for a condition by modulating at least a portion of the subject's autonomic nervous system by administering a first pharmacological agent together with at least one other, different pharmacological agent. The pharmacological agents may be concomitantly administered as described above, i.e., they may be given in close enough temporal proximity to allow their individual therapeutic effects to overlap. For example, embodiments of the subject invention may include the co-timely administration of a first pharmacological agent and at least a second, different pharmacological agent. By "co-timely" with respect to drug administration is meant administration of a second pharmacological agent for the treatment of a condition while a first pharmacological agent is still present in a subject's system at a therapeutically effective amount. It is to be understood that in some instances this will require sequential administration. Alternatively, multiple routes of administration may be employed, e.g., intravenous or subcutaneous injection of a first pharmacological agent may be combined with oral administration of a second, different pharmacological agent.

Embodiments may also include pharmaceutical compositions in unit dosage forms that are useful in treating conditions by modulating at least a portion of a subject's autonomic nervous system and which contain a first pharmacological agent and at least a second, different type of pharmacological agent. In other words, a single drug administration entity or single unit dosage form may include two or more pharmacological agents. For example, a single tablet, solution, capsule, dragee, trocheem suppository, syringe, transdermal patch, and the like, combining two or more pharmacological agents would be a unit dosage form. The therapeutic agents present in a unit dosage form may be present in amounts such that, upon administration of one or more unit doses of the composition, a subject may experience a longer lasting efficacy than with the administration of either agent alone. Such compositions may be included as part of a therapeutic package in which one or more unit doses are placed in a finished pharmaceutical container. Labeling may be included to provide directions for using the composition in the treatment of a condition by modulating at least a portion of a subject's autonomic nervous system. The actual amounts of each agent in such compositions will vary according to the specific compositions being utilized, the particular compositions formulated, the mode of application, the particular route of administration, and the like. Dosages for a given subject can be determined using conventional considerations, e.g., by customary comparison of the differential activities of the subject compositions and of a known agent, or by means of an appropriate, conventional pharmacological protocol. A person of ordinary skill in the art will be able without undue experimentation, having regard to that skill and this disclosure, to determine a therapeutically effective amount of a particular pharmacological agent for practice of this invention. For example, embodiments may include dosages conventionally administered for the particular pharmacological agents employed, where such dosages are known in the art.

Accordingly, in practicing the subject methods, an effective amount of a pharmacological agent is administered to a subject during at least one predetermined phase of the subject's menstrual cycle to treat a condition affecting the subject. As noted above, the particular dosage, mode of administration, treatment times, etc., will vary according to a variety of factors, but will generally fall within the ranges conventionally administered for the particular pharmacological agent employed. As noted above, the dose of pharmacological agent will be different for different subject, condition(s) treated, etc. Embodiments include determining the particular condition experienced by the subject and determining the appropriate pharmacological treatment regimen including dosage of particular agent(s) required to modulate at least a portion of the subject's autonomic nervous system in a manner effective to treat that subject for the particular condition.

The following descriptions of exemplary embodiments describe average doses and may vary. Such descriptions are for exemplary purposes only and are in no way intended to limit the scope of the invention. For example, the number of capsules or tablets, teaspoonfuls of solution, and the like, administered depends at least in part on the strength of the particular pharmacological agent administered. Furthermore, the number of doses administered each day, the time allowed between doses, and the length of time a subject takes the medicine, etc., depend on the condition being treated, i.e., the condition for which a subject is taking the pharmacological agent. Exemplary treatment protocols are now provided. The dose of pharmacological agent may be different for different subject, condition treated, etc. The following embodiments describe average doses and may vary. Such are for exemplary purposes only and are in no way intended to limit the scope of the invention. For example, the number of capsules or tablets, teaspoonfuls of solution, and the like, administered depends at least in part on the strength of the particular beta-blocker administered. Furthermore, the number of doses administered each day, the time allowed between doses, and the length of time a subject takes the medicine, etc., depend on the condition being treated, etc.

Beta-Blocker

As noted above, embodiments may include administering an effective amount of a beta-blocker to treat a condition. Such embodiments may include administering adult oral dosage forms (capsules and tablets) of acebutolol ranging from about 200 milligrams (mgs.) to about 1200 mgs., e.g., from about 200 mgs. to about 800 mgs. Such oral dosages may be administered as a single dose one time a day, two times a day, or divided into two daily doses for an adult, etc.

Embodiments may include administering atenolol to treat a condition. Such embodiments may include administering adult oral dosage forms (e.g., tablets) of atenolol (e.g., available under the brand name TENORMIN) that range from about 25 mgs. to about 100 mgs. once a day. For example, administration may include about 50 mgs. once a day, or about 100 mgs. of atenolol once a day, or about 50 mgs. atenolol two times a day, e.g., for about six to about nine days. Embodiments that include administering atenolol in adult injection dosage forms may include about 5 mgs. given over 5 minutes, repeated ten minutes later. Atenolol may also be administered intravenously in certain embodiments.

Embodiments may include administering adult oral dosage forms (e.g., tablets) of betaxolol to treat a condition. Such embodiments may include administering about 10 mgs. of betaxolol as an adult dosage form once a day.

Embodiments may include administering adult oral dosage forms (e.g., tablets) of bisoprolol (e.g., available under the brand name ZEBETA) to treat a condition. Such embodiments may include administering about 5 mgs. to about 10 mgs. of bisoprolol as an adult oral dosage forms (e.g., tablets) once a day.

Embodiments may include administering adult oral dosage forms (e.g., tablets) of carteolol to treat a condition. Adult oral dosage forms (e.g., tablets) of carteolol may include about 0.5 mgs. to about 10 mgs. administered once a day.

Embodiments may include administering esmolol to treat a condition via IV. esmolol may be administered via iv as follows: loading dose of about 20-30 mg ivp over 1 minute using a 10 mg/ml 10 ml vial and maintenance dose of about 2 To 12 mg/min as titrated to patient response and maintenance infusions may be increased by about 2 to 3 mg/min at 10 minute intervals until the desired response is achieved.

Embodiments may include administering adult oral dosage forms (e.g., tablets) of labetalol to treat a condition. Adult oral dosage forms (e.g., tablets) of labetalol may include about 100 mgs. to about 400 mgs. two times a day. Adult injection dosage forms may include about 20 mgs., e.g., injected slowly over about two minutes with additional injections of about 40 mgs. and about 80 mgs. given about every ten minutes if needed, up to a total of about 300 mgs., instead as an infusion at a rate of about 2 mgs. per minute to a total dose of about 50 mgs. to about 300 mgs.

Embodiments may include administering adult oral dosage forms (e.g., tablets) of metaprolol to treat a condition. Adult oral dosage forms (e.g., tablets) of metoprolol may include about 100 mgs. to 450 mgs. a day, taken as a single dose or in divided doses. For example, embodiments may include administering about 50 mgs. about every six hours for about 24 hours or more and then about 100 mgs. two times a day for about 1 to about 3 months or more, e.g., from about 1 to about 3 years or more. Embodiments may include administering long-acting adult oral dosage forms (extended-release tablets) that may include up to about 400 mgs. once a day. Adult injection dosage forms may include about 5 mgs. every two minutes for about three doses.

Embodiments may include administering adult oral dosage forms (e.g., tablets) of nadolol (e.g., available under the brand name CORGARD) to treat a condition. Embodiments ay include administering adult oral dosage forms (e.g., tablets) of nadolol that may include about 40 mgs. to about 320 mgs. once a day.

Embodiments may include administering adult oral dosage forms (e.g., tablets) of oxprenolol to treat a condition. Embodiments may include administering adult oral dosage forms (e.g., tablets) of oxprenolol (short-acting) that may include about 20 mgs. three times a day. Embodiments may include administering adult long-acting oral dosage forms (extended-release tablets) that may include about 120 mgs. to about 320 mgs. once a day.

Embodiments may include administering adult oral dosage forms (e.g., tablets) of pentbutolol to treat a condition. Embodiments may include administering adult oral dosage forms (e.g., tablets) of penbutolol that may include about 20 mgs. once a day.

Embodiments may include administering adult oral dosage forms (e.g., tablets) of pindolol to treat a condition. Embodiments may include administering adult oral dosage forms (e.g., tablets) of pindolol that may include about 5 mgs. two times a day—up to about 60 mgs. a day.

Embodiments may include administering adult oral dosage forms (e.g., tablets) of propranolol to treat a condition. Embodiments may include administering adult oral dosage forms (e.g., tablets) of propranolol that may include, for regular (short-acting) oral dosage forms (tablets and oral solution), about 80 mgs. to about 320 mgs. a day taken in two, three, or four divided doses up to about 640 mgs./day in certain embodiments. Embodiments may also include about 10 mgs. to about 40 mgs. three or four times a day for an adult and about 500 micrograms (0.5 mgs.) to about 4 mgs. per kilogram of body weight a day taken in divided doses for children. Embodiments may include administering long-acting adult oral dosage forms (extended-release capsules) that may include about 80 mgs. to about 320 mgs. once a day up to about 640 mgs. once a day. Embodiments may include administering adult injection dosage forms that range from about 1 mg. to about 3 mgs. given at a rate not greater than about 1 mg per minute. The dose may be repeated after about two minutes and again after about four hours if needed. Children may be administered about 10 mgs. to about 100 micrograms (0.01 to 0.1 mg) per kilogram of body weight given intravenously about every six to eight hours.

Embodiments may include administering adult oral dosage forms (e.g., tablets) of sotalol to treat a condition. Embodiments may include administering adult oral dosage forms (e.g., tablets) of sotalol that may include about 80 mgs. two times a day up to about 320 mgs. per day taken in two or three divided doses.

Embodiments may include administering adult oral dosage forms (e.g., tablets) of timolol (e.g., available under the brand name BLOCADREN) to treat a condition. Embodiments may include administering adult oral dosage forms (e.g., tablets) of timolol that may include about 10 mgs. two times a day up to about 60 mgs. per day taken as a single dose or in divided doses. For example, up to 30 mgs. once a day or in divided doses.

Aldosterone Antagonists

Embodiments may include administering an aldosterone antagonist to treat a condition in accordance with the subject invention. For example, embodiments may include administering adult oral dosage forms (e.g., tablets) of spironolactone that may range from about 50 mgs. to about 400 mgs. daily. Embodiments may include administering adult oral dosage forms (e.g., tablets) of eplerenone that may range from about 50 mgs. to about 100 mgs. daily.

Angiotensin II Receptor Blockades

Embodiments may include administering an angiotensin II receptor blockade to treat a condition in accordance with the subject invention. Such embodiments may include administering an adult oral dosage form of candesartan (e.g., ATACAND) to a subject to treat a condition. Exemplary treatment protocols may include administering about 2 mgs. to about 32 mgs. of candesarten daily (i.e., for a 24 hour interval), e.g., about 16 mgs. daily. Embodiments may include administering adult oral dosage forms of irbersarten (e.g., AVAPRO) to a subject to treat a condition. Exemplary treatment protocols may include administering about 75 mgs. to about 100 mgs. or more, e.g., up to about 300 mgs., of irbersarten daily. Embodiments may include administering adult oral dosage forms of losartan (e.g., COZAAR) to a subject to treat a condition. Exemplary treatment protocols may include administering about 25 mgs. to about 50 mgs. or more, e.g., 100 milligrams, of losarten orally once daily or twice daily. Embodiments may include administering adult oral dosage forms of telmisartin (e.g., MICARDIS) to a subject to treat a condition. Exemplary treatment protocols may include administering about 20 mgs. to about 80 mgs. of telmisartin daily. Embodiments may include administering adult oral dosage forms of valsartan (e.g., DIOVAN) to a subject to treat a condition. Exemplary treatment protocols may include administering about 20 mgs. to about 80 mgs. of valsarten once daily. Embodiments may include administering adult oral dosage forms of eprosarten (e.g., TEVETAN) to a subject to treat a condition. Exemplary treatment protocols may include administering about 400 mgs. to about 800 mgs. of eprosarten once daily or twice daily.

Angiotensin Converting Enzyme Inhibitors (ACE Inhibitors)

Embodiments may include administering an ACE inhibitor to a subject to treat a condition in accordance with the subject invention. Such may include administering adult oral dosage forms of captropil (e.g., CAPOTEN) to a subject to treat a condition. Exemplary treatment protocols may include administering about 12.5 mgs. to about 50 mgs. of captropil over about 8 to about 12 hours. Embodiments may include administering adult oral dosage forms of enalapril (e.g., VASOTEC) to a subject to treat a condition. Exemplary treatment protocols may include administering about 5 mgs. to about 20 mgs. of enalapril once daily. Embodiments may include administering adult oral dosage forms of fosinopril (e.g., MONOPRIL) to a subject to treat a condition. Exemplary treatment protocols may include administering about 10 mgs. to about 80 mgs., e.g., about 20 mgs. to about 40 mgs., of fosinopril daily. Embodiments may include administering adult oral dosage forms of lisinopril (e.g., PRINIVIL) to a subject to treat a condition. Exemplary treatment protocols may include administering about 10 mgs. to about 80 mgs., e.g., about 20 mgs. to about 40 mgs., of lisinopril daily. Embodiments may include administering adult oral dosage forms of moexipril (e.g., UNIVASC) to a subject to treat a condition. Exemplary treatment protocols may include administering about 3.75 mgs. to about 15 mgs., e.g., 7.5 mgs. of moexipril daily. Embodiments may include administering adult oral dosage forms of quinaapril (e.g., ACCUPRIL) to a subject to treat a condition. Exemplary treatment protocols may include administering about 10 mgs. to about 80 mgs, e.g., about 20 mgs., of quinapril once daily. Embodiments may include administering adult oral dosage forms of ramipril (e.g., ALTACE) to a subject to treat a condition. Exemplary treatment protocols may include administering about 2.5 mgs. to about 20 mgs. of ramipril daily. Embodiments may include administering adult oral dosage forms of trandolapril (e.g., MAVIK) to a subject to treat a condition. Exemplary treatment protocols may include administering about 1 mg. to about 4 mgs., e.g., about 2 mgs., of trandolapril daily.

Statins

Embodiments may include administering adult oral dosage forms (e.g., tablets) of a statin to treat a condition in accordance with the subject invention. For example, embodiments may include administering adult oral dosage forms (e.g., tablets) of atorvastatin (e.g., available under the brand name Lipitor) that may range from about 0.5 mgs. to about 80 mgs. daily. Embodiments may include administering adult oral dosage forms (e.g., tablets) of cerivastatin (e.g., available under the brand name Baycol) that may range from about 0.2 mgs. to about 0.3 mgs. daily. Embodiments may include administering adult oral dosage forms (e.g., tablets) of fluvastatin (e.g., available under the brand name lescoL) that may range from about 20 mgs. to about 80 mgs. daily. Embodiments may include administering adult oral dosage forms (e.g., tablets) of lovastatin (e.g., available under the brand name Mevacor) that may range from about 10 mgs. to about 80 mgs. daily. Embodiments may include administering adult oral dosage forms (e.g., tablets) of prevastatin (e.g., available under the brand name Pravachol) that may range from about 10 mgs. to about 40 mgs. daily. Embodiments may include administering adult oral dosage forms (e.g., tablets) of simvastatin (e.g., available under the brand name Zocor) that may range from about 5 mgs. to about 40 mgs. daily.

Triglycerides Lowering Drugs

Embodiments may include administering adult oral dosage forms (e.g., tablets) of a triglycerides lowering drug to treat a condition in accordance with the subject invention. For example, embodiments may include administering adult oral dosage forms (e.g., tablets) of fenofibrate (e.g., available under the brand name TRICOR) that may range from about 65 mgs. to about 200 mgs. daily. Embodiments may include administering adult oral dosage forms (e.g., tablets) of genfibrozil (e.g., available under the brand name LOPID) that may range from about 1200 mgs. total given as about 600 mgs. two times per day (e.g., every 12 hours).

Niacin

Embodiments may include administering niacin to treat a condition in accordance with the subject invention. For example, dosing may include administering by mouth about 2 mgs. to about 6 mgs. total, e.g., as given as about 1 mg. to about 2 mgs. twice per day or three times per day.

Diabetes Agents

Embodiments may include administering a diabetes drug to treat a condition in accordance with the subject invention. For example, embodiments may include administering adult oral dosage forms (e.g., tablets) of acarbose (e.g., available under the brand name PRECOSE) that may range from about 25 mgs. to about 300 mgs. for an eight hour interval. Embodiments may include administering adult oral dosage forms (e.g., tablets) of glimepiride (e.g., available under the brand name AMARYL) that may range from about 1 mg. to about 2 mgs. daily. Embodiments may include administering adult oral dosage forms (e.g., tablets) of glyburide (e.g., available under the brand names MICRONASE, DIABETA) that may range from about 1.5 mgs. to about 5 mgs. daily. Embodiments may include administering adult oral dosage forms (e.g., tablets) of metformin (e.g., available under the brand name GLUCOPHASGE) that may range from about 500 mgs. to about 850 mgs. for an 8 to 24 hour interval. Embodiments may include administering adult oral dosage forms (e.g., tablets) of miglitol (e.g., available under the brand name GLYCET) that may range from about 25 mgs. to about 100 mgs. for an 8 hour interval. Embodiments may include administering adult oral dosage forms (e.g., tablets) of pioglitazone (e.g., available under the brand name ACTOS) that may range from about 15 mgs. to about 40 mgs. daily. Embodiments may include administering adult oral dosage forms (e.g., tablets) of repaglinide (e.g., available under the brand name PRANDIN) that may range from about 0.5 mgs. to about 4.0 mgs. 3 times per day. Embodiments may include administering adult oral dosage forms (e.g., tablets) of rosiglitazone (e.g., available under the brand name AVANDIA) that may range from about 4 mgs. to about 8 mgs. daily.

Immunomodulators

Embodiments may include administering an immunomodulator to treat a condition in accordance with the subject invention. For example, embodiments may include administering interferon beta-1B (e.g., available under the brand name BETASERON), where dosing may include administering about 0.25 mg. subcutaneously every other day. Embodiments may also include administering interferon alfa-2A (e.g., available under the brand name ROFERON-A), where dosing may include administering about 3 million units to about 36 million units per day IM/SC to about 3 million units to about 36 million units 3 times per week (3 million units (1 ml); 6 million units/ml (3 ml); 0 million units/ml (0.9 ml), 3 ml); 36 million units/ml (1 ml)). Embodiments may also include administering interferon alfa-2B (e.g., available under the brand name INTRON-A), where dosing may include administering about 1 to about 30 million units/M2 IM/SC three times per week (3 million units (0.5 ml); 5 million units (0.5 ml); 10 million units (1 ml); 25 million units powder for injection: 18 million units and 50 million units). Embodiments may also include administering interferon alfa-2B and ribavirin combination pack (e.g., available under the brand name REBETRON), where dosing may include administering INTRON A at about 3 million units subcutaneously three times per week and about 500 mgs. to about 600 mgs. of ribavirin twice daily. Embodiments may also include administering interferon alfa-N3 (e.g., available under the brand name ALFERON N), where dosing may include administering about 250,000 units (0.05 ml) twice weekly (5 million units (1 ml)). Embodiments may also include administering interferon beta-1A (e.g., available under the brand name AVONEX), where dosing may include administering about 30 micrograms IM once weekly (reconstitute with 1.1 ml of diluent).

Nicotine

Embodiments may include administering nicotine to treat a condition in accordance with the subject invention. For example, embodiments may include administering nicotine in the form of chewing gum, e.g., from about 2 mgs. to about 4 mgs. dosage strength). Embodiments may include administering nicotine as an inhalant (e.g., about 4 mgs. per cartridge), nasal spray (e.g., each actuation of nicotine nasal spray may deliver about 0.5 mgs. nicotine), or as a transdermal system. For example, dosing schedules (mg/day) of nicotine transdermal systems may include a patch duration of about 24 hours and dosing schedule of about 7 mgs. to about 22 mgs. for about 2 to about 6 weeks; a patch duration of about 16 hours and a dosing schedule of about 15 mgs. for about 4 to about 12 weeks. Each dosing schedule may be followed by a reduced dosing schedule.

Sympathomimetics

Embodiments may include administering a sympathomimetic to treat a condition in accordance with the subject invention. For example, embodiments may include administering trimethaphan via an I.V., e.g., about 0.1 mgs. to about 1.0 mgs./minute, up to about 15 mgs. per minute. Embodiments may include administering by mouth clondine at about 0.1 mgs. to about 2.4 mgs. daily. Embodiments may include administering by mouth reserpine at about 10 mgs. to about 20 mgs. daily. Embodiments may include administering by mouth guanethidine at about 10 mgs. to about 50 mgs. daily.

Antihistamines

Embodiments may include administering adult oral dosage forms of an antihistamine to treat a condition in accordance with the subject invention. For example, embodiments may include administering adult oral-dosage forms (e.g., tablets) of BENADRYL at about 25 mgs. to about 50 mgs. three to four times daily. Nighttime dosage may include about 50 mgs. at bedtime.

Cholinergics

Embodiments may include administering a cholinergic to treat a condition in accordance with the subject invention. For example, embodiments may include administering bethanechol by mouth at about 10 mgs. to about 50 mgs. four times per day or three times per day. Embodiments may include administering methacoline as an inhaled aerosol at about 0.02 to about 25.0 mg/mL. Embodiments may include orally administering about 30 mgs. cevimeline three times per day.

Acetylcholinesterase Inhibitors

Embodiments may include administering an acetylcholinesterase inhibitor to treat a condition in accordance with the subject invention. For example, embodiments may include administering about 0.1 ml. to about 0.8 ml via an I.V. edrophonium or about 1 ml. of a 1:20000 solution (0.5 mg.) of neostigmine intramuscularly (IM) or subcutaneously (SC). Embodiments may also include orally administering about 5 mg of donepezil to about 10 mgs./day. Embodiments may also include administering about 1 to about 2 g of pralidoxime, e.g., as an infusion in 100 mL of saline, over about a 15 to 30 minute period, via I.V. About 16 mgs to about 32 mgs. of galanthamine may be administered orally twice per day. Physostigmine may be administered intravenously or intramuscularly e.g., about 0.5 mgs. to about 2 mgs. Rivastigmine may be orally administered, e.g., about 3 mgs. to about 6 mgs. two times per day.

Magnesium and Magnesium Sulfates

Embodiments may include administering magnesium to treat a condition in accordance with the subject invention. For example, a dose may include administering about 0.3 mEq/kg to about 1.0 meq mg/kg daily via an I.V.

Calcium Channel Blockers:

Embodiments may include administering a calcium channel blocker to treat a condition in accordance with the subject invention. Embodiments may include orally administering amlodipine besylate (e.g., available under the brand name NORVASC), e.g., about 5 mgs. to about 20 mgs. daily; diltiazem hydrochloride (e.g., available under the brand names CARDIZEM CD, CARDIZEM SR, DILACOR XR, TIAZAC) at about 30 mgs. to about 360 mgs. four times per day (for example 180 mgs. to about 360 mgs. divided into four times per day); felodipine plendil at about 2.5 mgs. to about 10 mgs. daily; isradipine (e.g., available under the brand names DYNACIRC, DYNACIRC CR) at about 2.5 mgs. daily; nicardipine (e.g., available under the brand name CARDENE SR) at about 20 mgs. to about 40 mgs. three times per day; nifedipine (e.g., available under the brand names ADALAT CC, PROCARDIA XL) at about 10 mgs. three times per day; nisoldipine (e.g., available under the brand name SULAR) at about 10 mgs. to about 20 mgs. daily; and verapamil hydrochloride (e.g., available under the brand names CALAN SR, COVERA HS, ISOPTIN SR, VERELAN) at about 40 mgs. three times per day.

Muscarinics

Embodiments may include administering a muscarinic to treat a condition in accordance with the subject invention. For example, embodiments may include administering about 5 mgs. of pilocarpine by mouth to a subject four times per day, up to about 30 mgs./day.

Sodium Channel Blockers

Embodiments may include administering a sodium channel blocker to treat a condition in accordance with the subject invention. For example, embodiments may include administering about 150 mgs. of propafenone by mouth every 8 hours (450 mgs./day) up to about 300 mgs. every 8 hours (90 mgs./day). Embodiments may also include administering about 50 mgs. to about 100 mgs. of flecainide by mouth about every 12 hours up to about 400 mgs./day. Embodiments may also include administering about 400 mgs. to about 2400 mgs. of tocainide by mouth about every 8 hours. Embodiments may also include administering about 100 mgs. to about 200 mgs. of phenytoin by mouth three times per day. Embodiments may also include administering about 10-30 mgs of about 1% to about 2% lidocaine IM (the maximum individual dosage typically should not exceed about 4.5 mg/kg of body weight and generally the maximum total dose should not exceed about 300 mgs.). Embodiments may also include administering about 150 mgs. to about 300 mgs. of dispoyramide by mouth about every 6 hours to about every 12 hours, up to about 1600 mgs. per day. Embodiments may also include administering quinidine (e.g., available under the brand name QUINAGLUTE) at about two tablets (648 mgs.; 403 mgs. of quinidine base) of QUINAGLUTE by mouth about every 8 hours.

Glucocorticoid Receptor Blockers

Embodiments may include administering a glucocorticoid receptor blocker to treat a condition in accordance with the subject invention. For example, embodiments may include administering mifepristone my mouth at about 400 micrograms to about 600 mgs.

Peripheral Andrenergic Inhibitors

Embodiments may include administering a peripheral andrenergic inhibitor to treat a condition in accordance with the subject invention. For example, embodiments may include administering about 5 mgs. to about 75 mgs. of guanadrel (e.g., available under the brand name HYLOREL) by mouth e.g., about 5 mgs. two times per day, about 20 to about 75 mgs. per day in divided doses. Embodiments may also include administering about 10 mgs. to about 50 mgs. or more per day of guanethidine monosulfate (e.g., available under the brand name ISMELIN) by mouth. Embodiments may also include administering about 0.05 to about 1.5 mgs. once per day by mouth of reserpine (e.g., available under the brand names SERPASIL, MECAMYLAMINE, HEXEMETHONIUM). Embodiments may also include administering about 2.5 mgs. of mecamylamine two times per day by mouth.

Blood Vessel Dilators

Embodiments may include administering a blood vessel dilator to treat a condition in accordance with the subject invention. For example, embodiments may include administering about 10 mgs. to about 50 mgs. of hydralazine hydrocholoride (e.g., available under the brand name APRESOLINE) by mouth four times a day. Embodiments may also include administering about 5 mgs. to about 40 mgs. of minoxidil (e.g., e.g., available under the brand name LONITEN) by mouth once per day.

Central Agonists

Embodiments may include administering a central agonist to treat a condition in accordance with the subject invention. For example, embodiments may include administering about 250 mgs. of alpha methyldopa (e.g., available under the brand name ALDOMET) by mouth three times per day or about 500 mgs. to about 2 grams per day divided into 2 to 4 doses. Embodiments may also include administering about 0.1 mgs. to about 0.6 mgs. of clonidine hydrochloride (e.g., available under the brand name CATAPRES) by mouth once per day. Embodiments may also include administering about 4 mgs. of guanabenz acetate (e.g., available under the brand name WYTENSIN) by mouth two times per day (up to about 32 mgs. per day). Embodiments may also include administering about 1 mg. to about 3 mgs. of guanfacine hydrochloride (e.g., available under the brand name TENEX) by mouth once per day.

Combined Alpha and Beta-Blockers

Embodiments may include administering a combined alpha and beta-blocker to treat a condition in accordance with the subject invention. For example, embodiments may include administering about 100 mgs. two times per day of labetolol hydrochloride (e.g., available under the brand names NORMODYNE, TRANDATE) by mouth up to about 400 mgs. per day. Embodiments may also include administering about 3.125 mgs. two times per day of carvedilol (e.g., available under the brand name COREG) by mouth up to about 50 mgs. per day.

Alpha Blockers

Embodiments may include administering an alpha and beta-blocker to treat a condition in accordance with the subject invention. For example, embodiments may include administering about 1 mg once per day by mouth of doxazosin mesylate (e.g., available under the brand name CARDURA) up to about 16 mgs. per day. Embodiments may also include administering about 0.5 mgs. by mouth of prazosin hydrochloride (e.g., available under the brand name MINIPRESS) two or three times per day (and may include about 6 to about 15 mgs. per day divided in 2 or 3 doses. Embodiments may also include administering about 1 mg. of terazosin hydrochloride (e.g., available under the brand name HYTRIN) by mouth once per day, up to about 5 mgs. per day.

Combination Diuretics

Embodiments may include administering a combined diuretic to treat a condition in accordance with the subject invention. For example, embodiments may include administering about 1-2 tablets of amiloride hydrochloride+hydrochlorothiazide (e.g., available under the brand name MODURETIC) once per day for tablets containing 5 mgs. of anhydrous amiloride HCl and 50 mgs. of hydrochlorothiazide). Embodiments may also include administering about 25 mgs. to about 50 mgs. once per day by mouth of spironolactone+hydrochlorothiazide (e.g., available under the brand name ALDACTAZIDE). Embodiments may also include administering about 1 to 2 tablets one per day of triamterene+ hydrochlorothiazide (e.g., available under the brand names DYAZIDE, MAXZIDE) for tablets containing 25 mgs. hydrochlorothiazide and 37.5 mgs. triaterene.

Potassium Sparing Diuretics

Embodiments may include administering a potassium sparing diuretic to treat a condition in accordance with the subject invention. For example, embodiments may include administering about 5 mgs. to about 20 mgs. by mouth once per day of amiloride hydrochloride (e.g., available under the brand name MIDAMAR). Embodiments may also include administering about 25 mgs. to about 200 mgs. once per day by mouth of spironolactone (e.g., available under the brand name ALDACTONE). Embodiments may also include administering about 1 to 2 tablets once per day of triamterene (e.g., available under the brand name DYRENIUM)) for tablets containing 25 mgs. hydrochlorothiazide and 37.5 mgs. triaterene.

Nitrates

Embodiments may include administering a nitrate to treat a condition in accordance with the subject invention. For example, embodiments may include administering isosorbide dinitrate (e.g., available under the brand name ISODIL) at about 50 to about 40 mgs. orally four times per day or 40 mgs. sustained release orally every 8 to 12 hours. Embodiments may also include administering isosorbide mononitrate (e.g., available under the brand names ISMO, MONOKET) at about 20 mgs. orally two times per day and/or may include administering extended release initially about 30 mgs. to about 60 mgs. orally once per day. Maximum of about 240 mgs./day. Embodiments may also include administering nitroglycerine ointment, e.g., about 0.5 inches q8h and/or about 0.5 to about 2 inches every 4 to 6 hours, maximum 4 inches every 4 to 6 hours (0.5 inches is about 7.5 mgs.). Embodiments may also include administering nitrobid, e.g., orally about 2.5 mgs. to about 9 mgs. 2 to 4 times per day. Embodiments may also include administering a nitroglycerin patch, e.g., one patch each day applied and removed at bedtime.

Cyclic Nucleotide Monophosphodiesterase ("PDE") Inhibitors

Embodiments may include administering a cyclic nucleotide monophosphodiesterase ("PDE") inhibitor to treat a condition in accordance with the subject invention. For example, embodiments may include administering about 5 mgs. to about 20 mgs. once per day of vardenafil (e.g., available under the brand name LEVITRA) by mouth. Embodiments may also include administering about 10 mgs. to about 20 mgs. of tadalafil (e.g., available under the brand name CIALIS) orally once per day. Embodiments may also include administering about 25 mgs. to about 100 mgs. of sildenafil (e.g., available under the brand name VIAGRA) orally once per day.

Alcohols

Embodiments may include administering an alcohol to treat a condition in accordance with the subject invention. For example, embodiments may include administering about 200 mgs. orally four times per day or 0.5 to about 1.0 ml per interspace for subarachnoid injections.

Vasopressin Inhibitors

Embodiments may include administering a vasopressin inhibitor to treat a condition in accordance with the subject invention. For example, embodiments may include administering about up to about 6.75 mg administered via IV of atosiban, e.g., −300 micrograms/min to about 100 micrograms/min IV.

Oxytocin Inhibitors

Embodiments may include administering an oxytoxin inhibitor to treat a condition in accordance with the subject invention. For example, embodiments may include administering about 0.25 to about IM of terbutaline, typically not more than about 0.5 mgs. within a four hour period. Embodiments may also include administering about 50 micrograms per minute IV of ritodrine, maximum dosage of about 300 micrograms per minute.

Glucagon Like Peptide 1

Embodiments may include administering glucagon like peptide 1 to treat a condition in accordance with the subject invention. For example, embodiments may include administering by I.V. about 200 µg/kg two times per day. Embodiments may also include administering by SQ infusion about 1.25 to about 20 µg/kg.

Relaxin Hormone

Embodiments may include administering a relaxin hormone to treat a condition in accordance with the subject invention. For example, embodiments may include administering 1 to 2 tablets of relaxin by mouth three times per day fro tablets pf valerian/ayrvedic passion flower blend (550 mgs.)

Renin Inhibitors

Embodiments may include administering a rennin inhibitor to treat a condition in accordance with the subject invention. For example, embodiments may include administering Aliskiren by mouth at about 2 mgs to about 10 mgs./day.

Estrogen and Analogues (e.g., Estradiols) and Metabolites

Embodiments may include administering estrogen and estrogen analogues and estrogen metabolites to treat a condition in accordance with the subject invention. For example, embodiments may include administering about 10 mgs. three times per day.

Gonadotropin-Releasing Hormone Inhibitors

Embodiments may include administering a gonadotropin-releasing hormone inhibitor to treat a condition in accordance with the subject invention. For example, embodiments may include administering leuprolide acetate at about 65 mgs. SQ (subcutaneous) implant.

Vesicular Monoamine Transport (VMAT) Inhibitors

Embodiments may include administering a VMAT inhibitor to treat a condition in accordance with the subject invention. For example, embodiments may include administering tetrabenazine by mouth at about 150 mgs. to about 200 mgs. once per day. Embodiments may also include administering reserpine at about 50 micrograms to about 500 micrograms one time per day.

Melatonin

Embodiments may include administering melatonin to treat a condition in accordance with the subject invention. For example, embodiments may include administering melatonin by mouth at about 0.5 mgs. to about 3.0 mgs. once per day.

Testosterone Inhibitors

Embodiments may include administering a testosterone inhibitor to treat a condition in accordance with the subject invention. For example, embodiments may include administering spironolactone by mouth at about 100 mgs. to about 300 mgs. in divided doses two times per day. Embodiments may include administering cyproterone acetate by mouth at about 100 mgs. to about 150 mgs. once per day.

Dipeptidyl Peptidase (DP) IV Inhibitors (DP4 Inhibitors)

Embodiments may include administering a DP4 inhibitor to treat a condition in accordance with the subject invention. For example, embodiments may include administering LAF237 by mouth at about 25 mgs. to about 200 mgs. per day.

Anti-Coagulants

Embodiments may include administering an anti-coagulant to treat a condition in accordance with the subject invention. For example, embodiments may include administering about 0.25 mg/kg intravensou bolus of abciximab and/or a continuous intravenous infusion of about 0.125 m g/kg/min (to a maximum of about 10 m g/min) for a period of time, e.g., 12 hours. Embodiments may include adminiserting dipridamole (e.g., AGGRENOX or the like) orally, e.g., one capsule twice daily. Embosiemnts may include administering anagrlide (e.g., AGRILYN or the like) orally, e.g., initially 0.5 mg orally four times daily or 1 mg orally twice daily or lowest effective dose- to a maximum 10 mg/day. Embodiments may include administering clopiogrel (e.g., PLAVIX or the like) at 75 mg orally once daily. Embodiments may include administering dipridamole (e.g., PERSANTINE or the like) at 75 to 100 mg orally four times daily. Embodiments may include administering eptifabatide (e.g., INTEGRILIN or the like) via IV at 0.5 mcg/kg/min to 180 mcg/kg or 135 mcg/kg and/or (e.g., followed by) 0.5 mcg/kg/min×20-24 hours. Fro example IV bolus of 180 mcg/kg over 1-2 minutes followed by 2 mcg/kg/min (maximum 15 mg/hr) up to 72 hours. Embodiments may include administering ticlopidine (e.g., TICLID or the like) at 250 mg orally twice daily. Embodiments may include administering tirofibam (e.g., AGGRASTAT or the like) at 0.4 mcg/kg/min to 0.1 mcg/kg/min. Embodiments may include administering ardeparin (e.g., NORMIFLO or the like) at 50 units SC every 12 hours. Embodiments may include administering dalteparin (e.g., FRAGMIN or the like) at 2500 units to 5000 units SC onc daily or 120 units/kg to about 10,000 SC every 12 hours. Embodiments may include administering enoxaparin (e.g., LOVENOX or the like) at 30-40 mg SC once daily. Embodiments may include administering lepiudin (e.g., REFLUDAN or the like) at 0.4 mg/kg (max weight of 110 kg) over al 5-20 seconds followed by does of 0.15 mg/kg/hr (max weight of 110 kg)×2-10 days as needed. Embodiments may include administering alteplase (e.g., ACTIVASE), t-PA or the like) at 15 mg to 35 mg via IV, e.g., 15 mg via IV bolus followed by 30-35 mg via IV over about 60 minutes. Embodiments may include administering reteplase (e.g., RETEVASE or the like) at 10.8 units IV over 2 minutes repeated in 30 minutes. Embodiments may include administering streptokinase at 1.5 million units IV over 60 minutes. Embodiments may include administering aminocaproic acid (e.g., AMICAR or the like) at 4 to 5 grams orally or IV over 1 hour, then 1 gram as needed. Embodiments may include administering cilostazol (e.g., PLETAL or the like) at 50 to 100 mg orally twice daily. Embodiments may include administering pentoxifylline (e.g., TRENTAL or the like) at 400 mg orally three times daily with meals.

Beta Agonists:

As described above, embodiments may include administering an effective amount of a beta agonist to a subject during at least one phase of the subject's menstrual cycle. Embodiments may include administering dosages of about 0.5 to about 1.0 micrograms/kilogram/minute of dobutamine intravenously, e.g., dosages of about 500 micrograms/ml to about 2000 micrograms/ml may be administered. Embodiments may include administering dosages of terbutaline at about 0.25 mg to about 0.5 mg intramuscularly ("IM"), e.g., not more than about 0.5 mg within a four hour period. Embodiments may include administering dosages of ritodrine at about 50 to about 350 micrograms per minute intravenously. Embodiments may include administering dosages of albuterol via nebulizer at about 0.5 ml of 0.5% inhalation solution with about 2.5 ml sterile saline solution given over about 5 to about 15 minutes three to four times per day. Embodiments may include administering dosages of metaproterenol via nebulizer every four hours wherein a vial containing 0.4% metaproterenol sulfate is equivalent to 0.2 ml of metaproterenol sulfate inhalation solution 5% diluted to 2.5 ml with normal saline.

Alpha Agonists:

As described above, embodiments may include administering an effective amount of an alpha agonist to a subject during at least one phase of the subject's menstrual cycle. Embodiments may include administering dosages of phenylephrine, e.g., subcutaneously or intramuscularly: from 1 mg to about 10 mg., wherein the initial dose generally should not exceed 5 mg.; intravenously: from about 0.1 mg to about 0.5 mg., wherein generally the initial dose should not exceed 0.5 mg. Injections are typically not repeated more often than about every 10 to 15 minutes. Embodiments may include administering dosages of metaraminol subcutaneously at about 2 to about 10 mg for an interval of about 10 minutes.

Prednisone and Steroids:

As described above, embodiments may include administering an effective amount of prednisone or a steroid to a subject during at least one phase of the subject's menstrual cycle. Embodiments may include administering dosages of prednisone or a steroid by mouth at about 5 to about 60 mg/day, once per day. For example, prednisone may be in the form of a solution, syrup or tablet and doses may be given once daily or every other day and about 2.5-15 mg may be taken by a subject 2-4 times daily.

Indirect Agents that Include Norepinephrine:

As described above, embodiments may include administering an effective amount of an indirect agents that include norepinephrine to a subject during at least one phase of the subject's menstrual cycle. Embodiments may include administering dosages of ephedrine IM or IV at about 25 to about 50 mg once per day. Embodiments may include administering dosages of phenylpropanolamine by mouth at about 25 mg every four hours, up to about 150 mg/day. Embodiments may include administering dosages of ampthetamine by mouth at about 2.5 mg to about 60 mg once per day.

Epinephrine:

As described above, embodiments may include administering an effective amount of epinephrine to a subject during at least one phase of the subject's menstrual cycle. Embodiments may include intravenously administering epinephrine at about 0.1 to about 0.25 mg (about 1 to about 2.5 ml of 1:10,000 solution) once every 20 to 30 minutes.

Norepinephrine:

As described above, embodiments may include administering an effective amount of norepinephrine to a subject during at least one phase of the subject's menstrual cycle. Embodiments may include intravenously administering norepinephrine at about 0.5 to about 1.0 mg (about 5 to about 10 ml of 1:10,000 solution) once every 5 minutes.

Potassium Channel Blockers and Magnesium Channel Blockers:

As described above, embodiments may include administering an effective amount of a potassium channel blocker or a magnesium channel blocker to a subject during at least one phase of the subject's menstrual cycle. Embodiments may include administering lithium by mouth at about 10 to about 60 mg/kg once per day. Embodiments may include administering valproate by mouth at about 10 to about 60 mg/kg once per day.

Acetylcholine

As described above, embodiments may include administering an effective amount of acetylcholine to a subject during at least one phase of the subject's menstrual cycle. Embodiments may include administering acetylcholine in the form of eye drops at about 0.75 to about 10 milligrams/ml acetylcholine.

Cocaine:

As described above, embodiments may include administering an effective amount of cocaine to a subject during at least one phase of the subject's menstrual cycle. Embodiments may include administering cocaine topically on mucus membranes, e.g., about 10% cocaine hydrochloride.

Amphetamines:

As described above, embodiments may include administering an effective amount of an amphetamine to a subject during at least one phase of the subject's menstrual cycle. Embodiments may include administering an amphetamine by mouth at about 5 to about 10 mg per day, e.g., 10 mg/day in divided doses.

Ephedrine:

As described above, embodiments may include administering an effective amount of ephedrine to a subject during at least one phase of the subject's menstrual cycle. Embodiments may include administering ephedrine sulfate injection at about 10 to about 50 mg injected subcutaneously or intramuscularly (equivalent to 0.2 to 1.0 ml of 5% solution).

Terbutaline:

As described above, embodiments may include administering an effective amount of terbutaline to a subject during at least one phase of the subject's menstrual cycle. Embodiments may include administering terbutaline intramuscularly at about 0.25 mg, e.g., one time, and typically not more than about 0.5 mg within a 4 hour period.

Dopamine:

As described above, embodiments may include administering an effective amount of dopamine to a subject during at least one phase of the subject's menstrual cycle. Embodiments may include administering dopamine intravenously at about 2 to about 50 microgram/kg/minute, wherein each milliliter of a 40 mg/ml preparation contains 40 mg of dopamine hydrochloride (equivalent to 32.31 mg of dopamine base). Embodiments may also include administering levodopa (L-dopa) in combination with carbidopa taken by mouth, e.g., about 25 mg carbidopa (up to about 2500 mg per day) and about 100 mg levodopa one half tablet, daily. Embodiments may also include administering bromocriptine (e.g., available under the brand name PARLODEL) by mouth at about 1.25 to about 100 mg per day.

Doputamine:

As described above, embodiments may include administering an effective amount of doputamine to a subject during at least one phase of the subject's menstrual cycle. Embodiments may include intravenously administering doputamine at about 0.5 to about 1.0 microgram/kg/min (up to about 500 microgram/ml).

Antidiuretic Hormone ("ADH") (Also Known as Vasopressin):

As described above, embodiments may include administering an effective amount of ADH to a subject during at least one phase of the subject's menstrual cycle. Embodiments may include subcutaneously or intramuscularly administering about 5 to about 10 units of AHD two or three times per day.

Oxytocin:

As described above, embodiments may include administering an effective amount of oxytocin to a subject during at least one phase of the subject's menstrual cycle. Embodiments may include intravenously administering oxytocin (e.g., available under the brand name PITOCIN) at about 1 to about 2 mU/mm (solution of 1 ml (10 units) combined with 1,000 ml of a non hydrating diluent).

THC Cannabinoids:

As described above, embodiments may include administering an effective amount of THC cannibinoid to a subject during at least one phase of the subject's menstrual cycle. Embodiments may include administering THC cannibinoid by rectal suppository at about 2.5 mg two times per day; or about 10 to about 20 mg one, two or three times per day by mouth; or 1 mg intravenously, e.g., one time; or about 200 mg once per day by mouth.

In certain embodiments, a given pharmacological agent may be administered at or near the time of a particular phase of a subject's menstrual cycle, i.e., in close temporal proximity to, including during, one or more predetermined phases of a subject's menstrual cycle. For example, embodiments of the subject methods may include administration of a pharmacological agent to achieve a particular parasympathetic activity/sympathetic activity ratio during at least a portion of the menses phase and/or follicular phase and/or the ovulation phase and/or the luteal phase. Of interest is the administration of a pharmacological agent at least near the time of, or during at least a portion of, the luteal phase and/or menses phase to modulate the autonomic nervous system to increase the parasympathetic activity/sympathetic activity ratio to treat the condition of interest. For example, embodiments may include determining the occurrence (predetermining the occurrence) of one or more phases of a subject's menstrual cycle, e.g., the luteal phase, and administering at least one pharmacological agent to increase the parasympathetic activity/sympathetic activity ratio during the one or more predetermined phases, e.g., during the luteal phase, after ovulation, or at a time prior to the start of the luteal phase and/or throughout all of or a portion of the luteal phase. Embodiments may include determining the occurrence of the menses phase and administering at least one pharmacological agent to increase the parasympathetic activity/sympathetic activity ratio during the menses phase, or at a time prior to the start of the menses phase and/or throughout all of or a portion of the menses phase. Similar treatment protocols may be employed for the follicular and ovulation phases.

The luteal phase is the part of the cycle that starts at ovulation and ends the day before a female's next period and usually lasts between about 12 to about 16 days. As such, embodiments of the subject invention may include administering an effective amount of a pharmacological agent at least one time during ovulation and/or at least one time during the luteal phase to increase the parasympathetic activity/sympathetic activity ratio in a manner effective to treat a condition, where embodiments may include administration during about all of the days of a subject's luteal phase or the late luteal phase. By "late luteal phase" is meant the later half of the luteal phase. For example, if a subject's luteal phase is determined to last about 14 days, the late luteal phase may be considered to be from about day 7 to about day 14 of the luteal phase.

As embodiments of the subject methods include administering an effective amount of at least one pharmacological agent to a subject during at least one predetermined menstrual phase, embodiments of the subject methods include determining the occurrence of the phases or at least one phase of a subject's menstrual cycle by any suitable method, e.g., using hormone-specific blood tests, urine tests, etc., as is known to those of skill in the art. For example, the onset of the luteal phase may be determined using a urine leutinizing hormone ("LH") detection test or kit, as are known in the art, e.g., as available under the brand names OVUQUICK ONE-STEP, CLEARPLAN EASY and SURESTEP. Other known methods may be employed as well and include empirical and non-empirical methods such as estimating the start, duration and/or end of a particular menstrual cycle phase, e.g., by a calendar method (counting days) or the like. Regardless of the particular method employed, in certain embodiments the onset of ovulation and/or the luteal phase and/or any other menstrual cycle phase may be determined and one or more of the pharmacological agents described above may be administered at or near the predetermined start of the subject's luteal phase and/or during at least part of a subject's determined luteal phase.

Electrical Modulation of at Least a Portion of the Autonomic Nervous System

As described above, embodiments of the subject invention may also include electrically modulating at least a portion of the autonomic nervous system to increase the parasympathetic activity/sympathetic activity ratio. By "electrically modulating at least a portion of a subject's autonomic nervous system" is meant altering or changing at least a portion of an autonomic nervous system by applying electrical energy to provide a change, alteration or shift in at least one component or aspect of the autonomic nervous system, as will be described in greater detail below. The electrical modulation of the autonomic nervous system may affect central motor output and/or nerve conduction and/or transmitter release and/or synaptic transmission and/or receptor activation, but in any event is a change that provides an increase in the parasympathetic activity/sympathetic activity ratio.

For example, embodiments may include electrically modulating at least a portion of a subject's autonomic nervous system to alter, shift or change the activity in at least one of the sympathetic system and parasympathetic system from a first state to a second state, where the second state is characterized at least by an increase or decrease in the parasympathetic activity/sympathetic activity ratio relative to the first state. Electrical energy may be employed to increase and/or decrease activity in at least a portion of the autonomic nervous system. For example, embodiments may include electrically modulating at least a portion of the autonomic nervous system to achieve one or more of the following (but in any event to achieve a net result of an increase or decrease in parasympathetic activity/sympathetic activity ratio, relative to the parasympathetic activity/sympathetic activity ratio prior to pharmacological modulation): (1) increasing activity in at least one parasympathetic nerve fiber to achieve an increase in activity in at least a portion of the parasympathetic system, (2) increasing activity in at least one sympathetic nerve fiber to achieve an increase in activity in at least a portion of the sympathetic system, (3) inhibiting activity in at least one parasympathetic nerve fiber to achieve a decrease in activity in at least a portion of the parasympathetic system, and (4) inhibiting activity in at least one sympathetic nerve fiber to achieve a decrease in activity in at least a portion of the sympathetic system. Certain embodiments of the subject invention may include electrically modulating the autonomic nervous system to both increase activity in at least a portion of the autonomic nervous system, e.g., increase activity in at least one parasympathetic nerve fiber, and inhibit activity in at least a portion of the autonomic nervous system, e.g., inhibit activity in at least one sympathetic nerve fiber, to treat a condition. Accordingly, embodiments of the subject methods include providing electrical energy to at least a portion of a subject's autonomic nervous system, where such electrical energy may be excitatory (to increase activity) or inhibitory (to decrease activity) and in certain embodiments may be both excitatory and inhibitory energies.

As noted above, electrical modulation in accordance with the subject invention may be performed prior to and/or at the same time and/or subsequent to any other medical or clinical treatment regime such as any of those described above, for example, pharmacological modulation of at least a portion of the subject's autonomic nervous system. In other words, the subject methods may include other, concomitant therapies or treatments to treat the same or different condition that do not employ electrical energy.

According to embodiments of the subject invention, electrical modulation is accomplished by at least administering electrical energy to a subject in a manner sufficient to treat the subject for a condition caused, precipitated or otherwise exacerbated, influenced or affected by the ratio of the parasympathetic activity/sympathetic activity ratio. In other words, activity in at least a portion of the autonomic nervous system is at a level that is at least contributing to or otherwise affecting or exacerbating a condition such a disease condition in need of treatment, and as such modulation of the autonomic nervous system may be employed to treat the condition.

Methods and devices suitable for use in electrically modulating a portion of subject's autonomic nervous system, and which may be employed in the practice of the subject invention, are described in detail in copending U.S. application Ser. No. 10/661,368, entitled "Treatment of Conditions Through Electrical Modulation of the Autonomic Nervous System", the disclosure of which is herein incorporated by reference.

In general, modulating at least a portion of the autonomic nervous system using electrical energy may be accomplished with the use of an electric energy applying devices (also referred to as electrical energy supplying or delivering devices), such as, e.g., described in the above-noted copending patent application. Once an electric energy applying device is positioned in a suitable position on or about one or more targeted areas of the autonomic nervous system such as one or more parasympathetic nerve fibers and/or one or more sympathetic nerve fibers, electrical energy is applied to the area(s) (e.g., the targeted nerve fiber(s)) for a period of time sufficient to provide the desired modulation of the autonomic nervous system. This period of time will vary depending on the area (e.g., the nerve fiber) being treated, the condition being treated, the particulars of the device used, etc.

As described in greater detail below, certain embodiments include simultaneously monitoring (i.e., in "real time") the parasympathetic activity and/or sympathetic activity such that electrical energy is applied until the desired increase in parasympathetic activity/sympathetic activity ratio is observed. Still further, in many embodiments once the desired ratio is achieved, electrical energy may be repeatedly applied thereto one or more times to maintain the desired state such that the subject methods may be repeated one or more times, i.e., the subject methods include chronic administration of electrical energy to at least one area of the autonomic nervous system. For example, in certain embodiments electrical energy (e.g., intermittent mild electrical pulses) may be delivered to a given area of the autonomic nervous system twenty-four hours a day for a period of days, weeks, months, years or even the entire lifetime of the subject in certain embodiments during one or more predetermined menstrual cycle phases. For example, electrical energy may be delivered to a given area during one or more predetermined phases of a subject's menstrual cycle such as during a predetermined luteal phase or the like every month for months, years or even the entire lifetime of the subject.

During the period of time that a given area of the autonomic nervous system is electrically modulated, the electrical energy may be applied substantially continuously, including continuously, or intermittently (i.e., pulsed or periodic), where in many embodiments the electrical energy is in the form of electrical pulses. In other words, in certain embodiments a given area of the autonomic nervous system (e.g., a given nerve fiber) may be continuously contacted with electrical energy during the above-described period of time and in certain other embodiments a given area of the autonomic nervous system (e.g., a given nerve fiber) may be pulsed or intermittently contacted with electrical energy during the period of time described above.

In accordance with embodiments of the subject methods to electrically modulate at least one area of the autonomic nervous system, once operatively positioned the electrical energy applying device is activated to provide an electrical signal to the targeted area such as to one or more nerve fiber(s) in a manner to increase or decrease the parasympathetic activity/sympathetic activity ratio at least in the particular area being contacted with electrically energy and in certain instances in adjacent areas or in the entire autonomic system, e.g., systemically in certain instances. For example, many nerve fibers are in close proximity and thus application of electrical energy to one nerve fiber may also increase or decrease activity in one or more other nerve fibers, e.g., nerve fibers in close proximity thereto.

In practicing the subject methods, activation of the electrical energy supplying device directly applies the electrical output of the device, i.e., electrical energy, to the targeted area. For example, electrodes may be positioned to direct electrical impulses to specific nerve fibers, etc. The exact parameters of the protocol may vary depending on the particular subject, condition being treated, etc. An electronic current wave may be provided when the electrical energy is applied. In certain embodiments, the current wave includes current waves of high frequency, e.g., high frequency pulses, where the current wave may also include low frequency amplitude modulation. In certain embodiments, a plurality of high frequency bursts of current pulses may be applied in addition to the application of underlying low frequency continuous stimulus. Monopolar or multipolar technologies may be employed.

For example, to increase activity in a portion of the autonomic nervous system, voltage or intensity may range from about 1 millivolt to about 1 volt or more, e.g., 0.1 volt to about 50 volts, e.g., from about 0.2 volt to about 20 volts and the frequency may range from about 1 Hz to about 2500 Hz, e.g., about 1 Hz to about 1000 Hz, e.g., from about 2 Hz to about 100 Hz in certain embodiments. In certain embodiments a pure d-c voltages may be employed. The pulse width may range from about 1 microsecond to about 2000 microseconds or more, e.g., from about 10 microseconds to about 2000 microseconds, e.g., from about 15 microseconds to about 1000 microseconds, e.g., from about 25 microseconds to about 1000 microseconds. The electrical output may be applied for at least about 1 millisecond or more, e.g., about 1 second, e.g., about several seconds, where in certain embodiments the stimulation may be applied for as long as about 1 minute or more, e.g., about several minutes or more, e.g., about 30 minutes or more may be used in certain embodiments.

To inhibit activity or conduction in a portion of the sympathetic nervous system, voltage or intensity may range from about 1 millivolt to about 1 volt or more, e.g., 0.1 volt to about 50 volts, e.g., from about 0.2 volt to about 20 volts and the frequency may range from about 1 Hz to about 2500 Hz, e.g., about 50 Hz to about 2500 Hz. In certain embodiments a pure d-c voltages may be employed. The pulse width may range from about 1 microseconds to about 2000 microseconds or more, e.g., from about 10 microseconds to about 2000 microseconds, e.g., from about 15 microseconds to about 1000 microseconds, e.g., from about 25 microseconds to about 1000 microseconds. The electrical energy may be applied for at least about 1 millisecond or more, e.g., about 1 second, e.g., about several seconds, where in certain embodiments the electrical energy may be applied for as long as about 1 minute or more, e.g., about several minutes or more, e.g., about 30 minutes or more may be used in certain embodiments.

The time period for modulating at least a portion of a subject's autonomic nervous system using electrical energy is analogous to that described above for pharmacologically modulating at least a portion of a subject's autonomic nervous system.

A variety of different devices for applying electrical energy to increase or inhibit activity in at least a portion of the autonomic nervous system in accordance with the subject invention may be employed as described in the above referenced, copending U.S. application Ser. No. 10/661,368, the disclosure of which is herein incorporated by reference. Electrical energy delivering devices that may be used to practice the subject invention may be positioned directly on a targeted area, e.g., positioned below the skin of a subject directly on or adjacent a portion of the autonomic nervous system (e.g., one or more nerve fibers) such as an implantable device, or may be an external device (i.e., some or all of the device may be external to the subject). In accordance with embodiments of the subject invention, one or more electrodes or electrical contacts may be positioned directly on or adjacent a targeted area of the autonomic nervous system, i.e., directly on or adjacent a portion of the parasympathetic and/or sympathetic system, where the one or more electrodes may be surgically implanted directly on or adjacent a targeted nerve fiber of a subject. In further describing the subject invention, a single electrode is described however it is to be understood that multiple electrodes may be employed and features and characteristics of the single electrode described herein are applicable to any other electrodes that may be employed in the practice of the subject invention.

Electrical energy delivering devices that may be employed in the practice of the subject methods typically include a stimulator (or inhibitor) such as an electrode, a controller or programmer and one or more connectors for connecting the stimulating device to the controller. In certain embodiments more than one electrode may be employed. In further describing representative electrodes, such are described in the singular, but it will be apparent that more than one electrode may be used, where such may be the same or may be different in one or more aspects. Accordingly, the description of a representative electrode suitable for use in the subject methods is applicable to other electrodes that may be employed.

The electrode employed in the subject invention is typically controllable to provide output signals that may be varied in voltage, frequency, pulse width, current and intensity. The electrode is typically one that provides both positive and negative current flow from the electrode and/or is capable of stopping current flow from the electrode and/or changing the direction of current flow from the electrode. For example, embodiments include an electrode that is controllable in these respects, i.e., controllable in regards to producing positive and negative current flow from the electrode, stop current flow from the electrode, change direction of current flow from the electrode, and the like. In certain embodiments, the electrode has the capacity for variable output, linear output and short pulse width.

The energy source for the electrical output is provided by a battery or generator such as a pulse generator that is operatively connected to the electrode. The energy source may be positioned in any suitable location such as adjacent to the electrode (e.g., implanted adjacent the electrode), or a remote site in or on the subject's body or away from the subject's body in a remote location and the electrode may then be connected to the remotely positioned energy source using wires, e.g., may be implanted at a site remote from the electrode or positioned outside the subject's body in certain instances. Implantable generators analogous to a cardiac pacemaker may be used in certain embodiments.

The electrode may be mono-polar, bipolar or multi-polar. In order to minimize the risk of an immune response triggered by the subject against the device and minimize damage such as corrosion and the like to the device from other biological fluids, etc., the electrode and any wires and optional housing materials are made of inert materials such as for example silicon, metal, plastic and the like. For example, a multi-polar electrode having about four exposed contacts (e.g., cylindrical contacts may be employed.

A variety of methods may be used to endoscopically or surgically implant the electrode on or adjacent at least a portion of the autonomic nervous system such as on or adjacent one or more nerve fibers of the parasympathetic nervous system and/or sympathetic system, where such methods are known to those of skill in the art. Because some nerve fibers may be in very close proximity to one another within a very small area, an analogous technique may generally be employed to provide operable placement of the electrode on or adjacent to any targeted area of the autonomic nervous system.

A controller or programmer is also typically included in an electrical energy supplying device. The programmer is typically one or more microprocessors under the control of a suitable software program. Other components of the programmer will be apparent to those of skill in the art, e.g., analog to digital converter, etc.

The electric energy supplying device employed in the practice of the subject methods may be pre-programmed for desired parameters. In many embodiments the parameters are controllable such that the electrode signal may be remotely modulated to desired settings without removal of the electrode from its targeted position. Remote control may be performed, e.g., using conventional telemetry with an implanted electric signal generator and battery, an implanted radiofrequency receiver coupled to an external transmitter, and the like. In certain embodiments, some or all parameters of the electrode may be controllable by the subject, e.g., without supervision by a physician. For example, a magnetic signal may be employed. In such embodiments, one or more magnets may be employed such that upon bringing a magnet in proximity to or away from the power source such as a pulse generator, the magnet may be employed to interfere with the electronic circuitry thus modulating the power—either increasing or decreasing the power supplied depending on whether the magnet is brought in proximity or moved away from the power source.

The present invention may be operated as an open-loop controlled system. In an open-loop system, the physician or patient may at any time manually or by the use of pumps or motorized elements adjust treatment parameters such as pulse amplitude, pulse width, pulse frequency, or duty cycle. Optionally, the present invention may incorporate a closed-loop control system which may automatically adjust the electrical parameters in response to a sensed symptom or an important related symptom indicative of the extent of the condition being treated. Under a closed-loop feedback system to provide automatic adjustment of parameters of the electrodes, a sensor that senses a condition of the body is utilized. In certain embodiments, such a condition may be a particular phase of the menstrual cycle (e.g., may sense hormonal changes or the like). More detailed descriptions of sensors that may be employed in the practice of the subject invention, and other examples of sensors and feedback control techniques that may be employed are disclosed in U.S. Pat. No. 5,716,377, which is incorporated herein by reference.

Operative placement of a suitable electric energy supplying device may be accomplished using any suitable technique. In general, such placement includes localization of an area of the autonomic nervous system, positioning the electrode on or adjacent the area and attaching the electrode to a power source. However, with regard to attaching the electrode to a power source, it should be understood that electrodes may be employed which make the implantation and/or attachment of a separate power source unnecessary. For example, an electrode may be employed which includes its own power source, e.g., which is capable of obtaining sufficient power for operation from surrounding tissues in the patient's body or which may be powered by bringing a power source external to the patient's body into contact with the patient's skin, or may include an integral power source, and the like. In such instances, the surgical procedure may be completed upon implantation of the electrode on or adjacent to the area of interest.

An electrode introducer needle may be employed to implant the electrode on or proximate to the area of interest. The size of the introducer needle may vary depending on the diameter of the electrode, etc., where in certain embodiments the electrode introducer needle may be a 12-gauge, 14-gauge, 16-gauge, 18-gauge, 20-gauge needle or 22-gauge needle, e.g., an electrode introducer needle available from Radionics in the Sluyter-Mehta kit as SMK 100 mm 2 mm active tip cannula. However, it should be understood that other electrode introducer needles may be used as appropriate to the needs and skill level of the practitioner performing the surgical procedure.

At least one imaging apparatus such as a CT scan, MRI apparatus, ultrasound apparatus, fluoroscope, or the like, may be employed to monitor the surgical procedure during the localization of a given area, e.g., to assist in determining a suitable entry point for the insertion of the electrode.

Once the entry point is determined, the skin overlying the entry point is shaved and prepared with antiseptic solution. A 25-gauge needle may be used to inject a subcutaneous local anesthetic (such as, for example, 2 cc of 2% lidocaine) into the skin and subcutaneous tissues overlying the entry point. In addition to the local anesthetic, the patient may be given intravenous sedation and prophylactic antibiotics prior to commencement of the implantation procedure if desired.

The electrode introducer needle is inserted at the entry point and advanced. The fluoroscope may be adjusted as the needle is advanced. Once the needle is suitably positioned, the stylet is withdrawn from the electrode introducer needle. A "test" electrode, if employed, used to test the placement of the electrode introducer needle may then be positioned within the central channel of the needle. If a "test" electrode is not employed, the electrode that is to be employed to modulate the autonomic nervous system may then be positioned within the central channel of the needle. The electrode may then be advanced to the distal tip of the needle to place the electrode on or proximate to the area of interest.

In certain embodiments, the "test" electrode, if employed, may be a radiofrequency stimulating electrode suitable to electrically stimulate the tissue at the end of the tip of the electrode and verify its position physiologically within the patient, which may be a different electrode than that ultimately implanted within the patient. A suitable radiofrequency stimulating electrode may be 10 cm with a 2-mm non-insulated active tip. Once the "test" electrode is inserted through the electrode introducer needle with its electrical contacts exposed, it may then be connected to an electrical stimulus/lesion generator for electrical stimulation.

The frequency of stimulation may be set at any suitable frequency, e.g., at about 50 Hz, and the voltage may be gradually increased until the subject reports acknowledgement of application of electrical current, e.g. reports stimulation, of or about the area of interest of the autonomic nervous system. Repositioning of the electrode may be performed as necessary.

If a "test" electrode is employed to test the placement of the electrode introducer needle and as such is different from the electrode to be employed to modulate the autonomic nervous system (i.e., the electrode to be implanted if it is desired to implant the electrode that will be employed to modulate the autonomic nervous system), the "test" electrode may then be removed from the electrode introducer needle while the needle is held firmly in place to prevent displacement. The electrode to be implanted may then be inserted through the central channel of the needle while the needle is held in place at the hub. Once the electrode to be implanted is in position, fluoroscopic imaging and electrical stimulation may be employed to verify the correct positioning of the needle and the electrode. Alternatively, if the electrode used to test the placement of the electrode introducer needle is the electrode to be implanted, the electrode may be left in the final test position.

Once the implanted electrode is in place, the end of the electrode that is outside the skin is carefully held in place against the skin. The electrode introducer needle may then be slowly removed, leaving the implanted electrode in place. At this point, if desired, a few small subcutaneous sutures may be placed around the electrode to hold it in the desired position.

Once the needle has been completely removed and the implanted electrode is in the final position, then the proximal part of the electrode that is coming out of the skin may be secured to the skin of the subject, e.g., by adhesive tape. Additionally, a small incision may be made on the skin at the area the electrode exits the body. Then several subcutaneous sutures may be placed around the electrode to hold it in place. The distal end of the electrode may then be connected to an extension wire or catheter, which is tunneled to the subclavicular area, or another region which will house the device used as an energy source for the implanted electrode. The device or devices used to control or stimulate the electrode may be surgically implanted in the desired region by procedures known in the art, such as have been applied in surgical neuromodulation therapies used to treat Parkinson's disease.

Electrical modulation may be performed at any suitable time, where such includes times analogous to those described above for pharmacological modulation. For example, electrical modulation may be performed at or near the time of a particular phase of a subject's menstrual cycle, i.e., in close temporal proximity to, including during, one or more predetermined phases of a subject's menstrual cycle. For example, embodiments of the subject methods may include electrically modulating at least a portion of a subject's autonomic nervous system to achieve a particular parasympathetic activity/sympathetic activity ratio (e.g., a normal ratio) during at least a portion of the menses phase and/or follicular phase and/or the ovulation phase and/or the luteal phase. Of interest is electrical modulation at least near the time of, or during at least a portion of, the luteal phase and/or menses phases to modulate the autonomic nervous system to increase or decrease the parasympathetic activity/sympathetic activity ratio. For example, embodiments may include electrical modulation of at least a portion of the autonomic nervous system to increase the parasympathetic activity/sympathetic activity ratio during the luteal phase, after ovulation. For example, embodiments may include determining the occurrence of one or more phases of a subject's menstrual cycle, e.g., the luteal phase, and applying electrical energy to at least a portion of the autonomic nervous system to increase the parasympathetic activity/sympathetic activity ratio during the one or more predetermined phases, e.g., during the luteal phase, or at a time prior to the start of the luteal phase and/or throughout all of or a portion of the luteal phase. Embodiments may include determining the occurrence of the menses phase and applying electrical energy to increase the parasympathetic activity/sympathetic activity ratio during the menses phase, or at a time prior to the start of the menses phase and/or throughout all of or a portion of the menses phase. Similar treatment protocols may be employed for the follicular and ovulation phases.

Embodiments of the subject invention may include electrically modulating at least a portion of a subject's autonomic nervous system at least one time during at least one predetermined menstrual cycle phase to increase or decrease the parasympathetic activity/sympathetic activity ratio, where embodiments may include electrically modulating at least a portion of a subject's autonomic nervous system during about all of the days of a subject's luteal phase and/or menses phase. In such instances, the subject methods typically include determining the occurrence of one or more phases of a subject's menstrual cycle by any suitable method as described above, e.g., using hormone-specific blood tests, urine tests, etc., as is known to those of skill in the art. For example, the onset of the luteal phase may be determined using a urine leutinizing hormone ("LH") detection test or kit, as are known in the art, e.g., as available under the brand names OVUQUICK ONE-STEP, CLEARPLAN EASY and SURESTEP. Other known methods may be employed as well and include empirical and non-empirical methods such as estimating the start, duration and/or end of a particular menstrual cycle phase, e.g., by a calendar method (counting days) or the like. Regardless of the particular method employed, the occurrence of one or more menstrual cycle phases may be determined and electrical modulation at least a portion of the subject's autonomic nervous system as described above may be performed at or near the determined start of the subject's determined menstrual cycle phase.

Regardless of how the autonomic nervous system is modulated (pharmacologically, electrically, etc.), certain embodiments of the subject methods may also include detecting, monitoring, observing, etc., information related to one or more aspects of the autonomic nervous system such as a physical and/or chemical aspect, e.g., activity, balance, etc., in at least a portion of the autonomic nervous system, e.g., in at least a portion of the sympathetic nervous system and/or parasympathetic system, and evaluating this information to determine the state of the autonomic nervous system, e.g., the parasympathetic activity and/or sympathetic activity. Once the state of the autonomic nervous system is determined, it may be evaluated in regards to whether the autonomic nervous system is in need of modulation, i.e., whether the parasympathetic activity/sympathetic activity ratio needs to be increased to treat a condition such that this analysis may be employed as a "trigger" to modulating or further modulating at least a portion of the autonomic nervous system wherein modulation may not be otherwise performed unless the analysis determined such is necessary.

Accordingly, collecting and evaluating this type of data and relating it to whether autonomic nervous system modulation is required may be employed as a "trigger" to pharmacologically modulating at least a portion of the autonomic nervous system (e.g., performed prior to, during or following a particular autonomic nervous system modulation protocol whether performed using pharmacological methods, electrical energy methods or other methods) such that such data may indicate whether, when, etc., modulation is required—if at all. For example, in certain embodiments modulation of at least a portion of a subject's autonomic nervous system may not be performed unless one or more aspects of the autonomic nervous system are detected and indicate such modulation is necessary. Any suitable physical and/or chemical aspect or indicator of the autonomic nervous system may be employed, e.g., amounts of T helper cells (Th1 and/or Th2), conduction, catecholamine levels, heart rate variability ("HRV"), respiratory sinus arrhythmia, action potentials, QT interval, as well as chronotropic, inotropic, and vasodilator responses. For example, in certain embodiments HRV measures such as low frequency peak ("LF"), high frequency peak ("HF"), and the LF/HF ratio may be used as indicators of different aspects of the autonomic nervous system. Typically, in normal females, normalized units ("NU") of LF and LF/HF ratio are higher, and NU of HF are lower, during the luteal phase. In certain embodiments, particular hormonal levels, e.g., associated with a particular phase of the menstrual cycle, may be detected. In certain embodiments, detection may include detecting the activity or function of a particular organ or system under the control of the autonomic nervous system. Other exemplary measurements may include, but are not limited to, plasma volume, effective renal plasma volume, effective renal blood flow, norepinephrine, and concentrations of rennin-angiotensin-aldosterone system hormones, which have been noted to be higher during the luteal phase than in the follicular phase. Any suitable detection means may be employed to detect relevant information about the autonomic nervous system.

In certain embodiments, a control feedback loop is provided. For example, during or following a particular treatment regimen, the sympathetic activity and/or parasympathetic activity may be monitored, observed, detected, etc., e.g., by sensing conduction in at least a portion of the sympathetic system and/or parasympathetic system by any suitable method. Other methods that may be employed to monitor the autonomic system include, but are not limited to, amounts of T helper cells (Th1 and/or Th2), neurography, continuous or serial measurements of circulating catecholamine levels, chronotropic, inotropic, and vasodilator responses, heart rate variability ("HRV"), particular hormonal levels, e.g., associated with a particular phase of the menstrual cycle, postganglionic action potentials, QT interval, and the like. For example, in certain embodiments HRV measures such as low frequency peak ("LF"), high frequency peak ("HF"), and the LF/HF ratio may be used to monitor the autonomic nervous system, as well as, but not limited to, plasma volume, effective renal plasma volume, effective renal blood flow, norepinephrine, and concentrations of rennin-angiotensin-aldosterone system hormones. For example, a sensor suitable for detecting nerve cell or axon activity that are related to the autonomic nervous system may be implanted in a portion of a subject's body. A sensor may take the form of an electrode or the like. Signals received by such a sensor may be amplified before further processing. A sensor may also take the form of a device capable of detecting nerve compound action potentials or may take the form of a transducer that includes an electrode with an ion selective coating applied which is capable of directly transducing the amount of a particular transmitter substance or its breakdown by-products.

Embodiments include utilizing a feedback system in such a manner that, if the desired increase/decrease in sympathetic and/or parasympathetic activity is not achieved, the same or a different treatment protocol for modulating the activity of the autonomic nervous system activity may be performed. For example, in those instances where a different modulation protocol is performed from a first modulation protocol, one or more of the treatment parameters may be modified. For example, if a first modulation protocol included pharmacological modulation, a second, different modulation protocol may be employed, e.g., a different pharmacological agent may be employed instead or in addition to the first, where the differences may include dosage, type, mode of administration, etc., or the second protocol may include an electrical modulation protocol. In those instances where a different protocol is performed from a first, electrical energy modulation protocol, one or more of the treatment parameters may be modified for a second, different electrical modulation protocol, e.g., a different electrical energy protocol may be employed instead of or in addition to the first, where the differences may include voltage, frequency, pulse width, etc., or the second protocol may include a pharmacological modulation protocol.

Certain embodiments may include simultaneously monitoring, detecting, observing, etc., (i.e., in "real time") the sympathetic activity and/or parasympathetic activity such that modulation of at least a portion of the autonomic nervous system may be performed to treat a condition and the result of the modulation may be observed and/or monitored, e.g., at least once, continuously or intermittently or periodically and in certain embodiments until the desired increase or inhibition in activity is observed or longer. Still further, in many embodiments once the desired autonomic nervous system modulation is achieved the same or different modulation treatment protocol may be performed thereafter at least one time and may be for a period of time, e.g., one or more times, to maintain the desired state such that embodiments of the subject methods may be repeated one or more times.

The above-described methods find use in a variety of different applications, representative types of which are described in greater detail below.

Utility

The subject methods find use in a variety of applications in which it is desired to treat a subject for a condition at least suspected of being exacerbated during at least one menstrual cycle phase. Such conditions may be referred to as conditions that have catamenial variations. In accordance with embodiments of the subject invention, at least a portion of a subject's autonomic nervous system is modulated to increase the parasympathetic activity/sympathetic activity ratio in a manner sufficient to treat the subject for the condition. In accordance with embodiments of the subject invention, at least a portion of a subject's autonomic nervous system is modulated to decrease the parasympathetic activity/sympathetic activity ratio in a manner sufficient to treat the subject for the condition.

The subject methods find use in the treatment of a variety of different conditions, including, but not limited to, cardiovascular conditions including cardiovascular disease, e.g., atherosclerosis, coronary artery disease, hypertension, hyperlipidemia, eclampsia, pre-eclampsia, cardiomyopathy, volume retention, congestive heart failure, QT interval prolongation, aortic dissection, aortic aneurysm, arterial aneurysm, arterial vasospasm, myocardial infarction, reperfusion syndrome, ischemia, sudden adult death syndrome, arrhythmia, fatal arrythmias, coronary syndromes, coronary vasospasm, sick sinus syndrome, bradycardia, tachycardia, thromboembolic disease, deep vein thrombosis, coagulopathy, disseminated intravascular coagulation ("DIC"), mesenteric ischemia, syncope, venous thrombosis, arterial thrombosis, malignant hypertension, secondary hypertension, primary pulmonary hypertension, secondary pulmonary hypertension, raynaud's, paroxysmal supraventricular tachycardia, and the like; neurodegenerative conditions including neurodegenerative diseases, e.g., Alzheimer's Disease, Pick's Disease, Parkinson's Disease, dementia, delirium, amyotrophic lateral sclerosis, and the like; neuroinflammatory conditions including neuroinflammatory diseases, e.g., viral meningitis, viral encephalitis, fungal meningitis, fungal encephalitis, multiple sclerosis, charcot joint, schizophrenia, myasthenia gravis, and the like; orthopedic inflammatory conditions including orthopedic inflammatory diseases, e.g., osteoarthritis, inflammatory arthritis, regional idiopathic osteoporosis, reflex sympathetic dystrophy, Paget's disease, osteoporosis, antigen-induced arthritis, juvenile chronic arthritis, and the like; lymphoproliferative conditions including lymphoproliferative diseases, e.g., lymphoma, lymphoproliferative disease, Hodgkin's disease, inflammatory pseudomotor of the liver, and the like; autoimmune conditions including autoimmmune diseases, e.g., Graves disease, raynaud's, hashimoto's, takayasu's disease, kawasaki's diseases, arteritis, scleroderma, CREST syndrome, allergies, dermatitis, Henoch-schlonlein purpura, goodpasture syndrome, autoimmune thyroiditis, myasthenia gravis, Reiter's disease, lupus, and the like; inflammatory conditions, e.g., acute respiratory distress syndrome ("ARDS"), multiple sclerosis, rheumatoid arthritis, juvenile rheumatoid arthritis, juvenile chronic arthritis, migraines, chronic headaches, and the like; infectious diseases, e.g., sepsis, viral and fungal infections, diseases of wound healing, wound healing, tuberculosis, infection, AIDS, human immunodeficiency virus, and the like; pulmonary conditions including pulmonary diseases, e.g., tachypnea, fibrotic lung diseases such as cystic fibrosis and the like, interstitial lung disease, desquamative interstitial pneumonitis, non-specific interstitial pneumonitis, lymphocytic interstitial pneumonitis, usual interstitial pneumonitis, idiopathic pulmonary fibrosis, pulmonary edema, aspiration, asphyxiation, pneumothorax, right-to-left shunts, left-to-right shunts, respiratory failure, and the like; transplant-related conditions such as transplant related side effects such as transplant rejection, transplant-related tachycardia, transplant related renal failure, transplant related bowel dysmotility, transplant-related hyperreninemia, and the like; gastrointestinal conditions including gastrointestinal diseases, e.g., hepatitis, xerostomia, bowel mobility, peptic ulcer disease, constipation, ileus, irritable bowel syndrome, post-operative bowel dysmotility, inflammatory bowel disease, typhilitis, cholelethiasis, cholestasis, fecal incontinence, cyclic vomiting syndrome, and the like; endocrine conditions including endocrine diseases, e.g., hypothyroidism, hyperglycemia, diabetes, obesity, syndrome X, insulin resistance, polycycstic ovarian syndrome ("PCOS"), and the like; genitourinary conditions including genitourinary diseases, e.g., bladder dysfunction, renal failure, hyperreninemia, hepatorenal syndrome, pulmonary renal syndrome, incontinence, arousal disorder, menopausal mood disorder, premenstrual mood disorder, renal tubular acidosis, pulmonary renal syndrome, and the like; skin conditions including skin diseases, e.g., wrinkles, cutaneous vasculitis, psoriasis, and the like; aging associated conditions including aging associated diseases, e.g., shy dragers, multi-system atrophy, age related inflammation conditions, cancer, aging, and the like; neurologic conditions including neurologic diseases such as epilepsy, depression, schizophrenia, seizures, stroke, insomnia, cerebral vascular accident, transient ischemic attacks, stress, bipolar disorder, concussions, post-concussive syndrome, cerebral vascular vasospasm, central sleep apnea, obstructive sleep apnea, sleep disorders, headaches incuding chronic headaches, migraines, acute disseminated encephalomyelitis ("ADEM"), and the like; Th-2 dominant conditions including Th-2 dominant diseases, e.g., typhilitis, osteoporosis, lymphoma, myasthenia gravis, lupus, and the like; conditions, including diseases, that cause hypoxia, hypercarbia, hypercapnia, acidosis, acidemia, e.g., ventilation/perfusion (V/Q) mismatch, Chronic Obstructive Pulmonary Disease ("COPD"), emphysema, any chronic lung disease that causes acidosis, acute pulmonary embolism, sudden adult death syndrome ("SADS"), chronic pulmonary embolism, pleural effusion, cardiogenic pulmonary edema, non-cardiogenic pulmonary edema, acute respiratory distress syndrome (ARDS), neurogenic edema, hypercapnia, acidemia, asthma, renal tubular, asthma, acidosis, chronic lung diseases that cause hypoxia, hypercarbia or hypercapnia, and the like; OB-GYN conditions including OB-GYN diseases, e.g., amniotic fluid embolism, menopausal mood disorders, premenstrual mood disorders, pregnancy-related arrhythmias, fetal stress syndrome, fetal hypoxia, amniotic fluid embolism, gestational diabetes, pre-term labor, cervical incompetence, fetal distress, peri-partum maternal mortality, peripartum cardiomyopathy, labor complications, premenstrual syndrome, dysmenorrheal, endometriosis, fertility and subfertility conditions such as infertility, early pregnancy loss, spontaneous abortion, subfertility, failure of implantation, amenorrhea, luteal insufficiency, and the like; sudden death syndromes, e.g., sudden adult death syndrome, and the like; menstrual related disorders, e.g., pelvic pain, dysmenorrheal, gastrointestinal disease, nausea, and the like; peripartum and pregnancy related conditions, e.g., peripartum cardiomyopathy, and the like; fibrosis; post-operative recovery conditions such as post-operative pain, post operative ileus, post-operative fever, post-operative nausea, and the like; post-procedural recovery conditions such as post-procedural pain, post procedural ileus, post-procedural fever, post-procedural nausea, and the like; chronic pain; trauma; hospitalization; glaucoma; disorders of thermoregulation; fibromyalgia; and the like. Other conditions may also be treated in accordance with the subject invention. Embodiments of the subject invention include treating one or more conditions, sequentially or at the same time, in accordance with the subject invention.

By "treatment" is meant that at least an amelioration of the symptoms associated with the condition afflicting the subject is achieved, where amelioration is used in a broad sense to refer to at least a reduction in the magnitude of a parameter, e.g., symptom, associated with the condition being treated. As such, treatment also includes situations where the condition, or at least symptoms associated therewith, are completely inhibited, e.g., prevented from happening, or stopped, e.g. terminated, such that the subject no longer suffers from the condition, or at least the symptoms that characterize the condition.

A variety of subjects are treatable according to the subject methods. In many embodiments the subjects are "mammals" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subjects are humans and particularly female humans. While the present invention may be used for the treatment of a human, female subject, it is to be understood that the subject methods may also be carried-out on other female animal subjects such as, but not limited to, mice, rats, dogs, cats, livestock and horses, etc. Accordingly, it is to be understood that any female subject in need of being treated according to the subject invention is suitable.

Moreover, suitable subjects of this invention include those who have and those who have not previously been afflicted with a condition, those that have previously been determined to be at risk of suffering from a condition, and those who have been initially diagnosed or identified as being afflicted with or experiencing a condition.

Devices and Systems

The subject invention also includes devices and systems that may be employed in the practice of the subject methods. The subject systems may include an effective amount of at least pharmacological agent. The pharmacological agent may be in any suitable formulation or form. For example, a system may include a pharmacological composition for transdermal administration, e.g., present as an active agent of a transdermal patch, film or the like, an oral dosage form, injection dosage form, suppository, etc.

In certain embodiments, the subject systems may also include suitable pharmacological agent delivery means, the particulars of which may be dictated by the particular pharmacological agent employed, e.g., the particular form of the agent such as whether the pharmacological agent is formulated into preparations in solid, semi-solid, liquid or gaseous forms, such as tablets, capsules, powders, granules, ointments, solutions, suppositories, injections, inhalants and aerosols, and the like, and the particular mode of administration of the agent, e.g., whether oral, buccal, rectal, parenteral, intraperiactivityal, intradermal, transdermal, intracheal, intravaginal, endocervical, intrathecal, intranasal, intravesicular, on the eye, in the ear canal, etc. Accordingly, certain systems may include a suitable drug delivery device, e.g., a suppository applicator, syringe, I.V. bag and tubing, electrode, an implantable drug delivery device, an electrostimulatory device, and the like.

Systems may also include one or more devices for delivering, e.g., implanting, a component such as a drug delivery device, an electrosurgical device, and the like, to a target site of a subject such as into the body cavity of a subject. For example, an endoscope, introducer needle, and the like, may be provided. Systems may also include one or more imaging or scanning apparatuses such as a fluoroscope, CT scan, and the like.

Embodiments of the subject systems may also include an electrical energy supplying device such that a system according to the present invention may include at least one electrode for electrically modulating at least a portion of a subject's autonomic nervous system. In certain embodiments the electrical energy supplying device may be an implantable device, or at least certain components such as one or more electrodes, may be implantable. Certain embodiments may include a plurality of electrodes, where some or all may be the same or some or all may be different. For example, at least a first electrode may be provide for electrically stimulating at least a portion of the autonomic nervous system and at least a second electrode may be provided for inhibiting activity in at least a portion of the autonomic nervous system. In certain embodiments, a "test" electrode, as described above, may be included in a system. As noted above, such "test" electrodes may be a radiofrequency controlled electrode. Still further, one or more electrodes may be included in a system which, instead of or in addition to delivering electric impulses to at least a portion of the autonomic nervous system, delivers an autonomic nervous system pharmacological agent to at least a portion of the autonomic nervous system, e.g., may be used to deliver a pharmacological agent. Included may be an energy source such as a battery or generator, where in certain embodiments the energy source may be implantable, and may also include one or more leads or wires for coupling the one or more electrodes to an energy source.

A system for use in practicing the subject methods may also include a suitable detector for detecting one or more physical and/or chemical aspects related to the autonomic nervous system. The detector at least includes data gathering means. Also provided may be data analysis means where such may be a separate component from or integral with data gathering means, but in many embodiments is operatively coupled to data gathering means, e.g., integral with. In use, data related to one or more aspects of the autonomic nervous system may be collected by data gathering means and forwarded to data analysis means which executes steps necessary to process and evaluate the collected data and determine whether at least a portion of the autonomic nervous system is in need of modulation. Such evaluation may include comparing data to reference values, etc. For example, reference values may represent normal parasympathetic activity/sympathetic activity ratios, as described above, such as parasympathetic activity/sympathetic activity ratios of healthy, like women in a particular menstrual cycle phase and/or parasympathetic activity/sympathetic activity ratios of the subject during a particular menstrual cycle phase, typically one in which the condition of interest is not exacerbated or, if the phase is the same phase in which the condition is observed to be exacerbated, there is no observable exacerbation at the time the ratio is observed for use as a reference data point.

When present, a detector (or data evaluation means if separate) may be operatively coupled to one or more other elements of a given drug delivery means and/or electrical energy supplying device such that results of the determinations of autonomic modulation may automatically trigger (or cease) activation of drug delivery and/or electrical energy to the autonomic nervous system. Suitable detectors include any detector capable of gathering information about the autonomic nervous system and includes both invasive, minimally invasive and non-invasive detectors where in certain embodiments a detector may be an implantable detector. Suitable detectors include, but are not limited to, those capable of collecting data regarding nerve conduction, circulating catecholamine levels, heart rate variability ("HRV"), respiratory sinus arrhythmia, post-ganglionic action potentials, QT interval, and the like and include, but are not limited to, MRI apparatuses, CT apparatus, hormone level detectors, neurography apparatuses, cardiovascular monitors, sensors including electrodes, etc.

Computer Readable Mediums and Programming Stored Thereon

Any part of the subject methods, e.g., detection, analysis and activation/termination of drug delivery and/or electrical energy including selecting suitable drug delivery parameters and/or electrical parameters, may be performed manually or automatically. For example, the subject invention may include suitable computing means such as suitable hardware/ software for performing one or more aspects of the subject methods. For example, one or more aspects of the subject invention may be in the form of computer readable media having programming stored thereon for implementing the subject methods. Accordingly, programming according to the subject invention may be recorded on computer-readable media, e.g., any medium that can be read and accessed directly or indirectly by a computer. Such media include, but are not limited to, computer disk or CD, a floppy disc, a magnetic "hard card", a server, magnetic tape, optical storage such as CD-ROM and DVD, electrical storage media such as RAM and ROM, and the hybrids of these categories such as magnetic/optical storage media. One of skill in the art can readily appreciate how any of the presently known computer readable mediums may be used to provide a manufacture that includes a recording of the present programming/algorithm for carrying out the above-described methodology. Thus, the computer readable media may be, for example, in the form of any of the above-described media or any other computer readable media capable of containing programming, stored electronically, magnetically, optically or by other means. As such, stored programming embodying steps for carrying-out some or all of the subject methods may be transferred to a computer-operated apparatus such as a personal computer (PC) or the like, by physical transfer of a CD, floppy disk, or like medium, or may be transferred using a computer network, server, or other interface connection, e.g., the Internet.

For example, the subject invention may include a computer readable medium that includes stored programming embodying an algorithm for carrying out some or all of the subject methods, where such an algorithm is used to direct a processor or series of processors to execute the steps necessary to perform the task(s) required of it and as such in certain embodiments the subject invention includes a computer-based system for carrying-out some or all of the subject methods. For example, such a stored algorithm may be configured to, or otherwise be capable of, directing a microprocessor to receive information directly or indirectly from data gathering means (i.e., information collected by data gathering means about the autonomic nervous system) and process that information to determine the state of the autonomic nervous system, e.g., the activity level of the parasympathetic system and/or the sympathetic system and even whether the autonomic nervous system requires modulation and, if so, the specifics of the modulation that may be required, e.g., to treat a condition. The result of that processing may be communicated to a user, e.g., via audio and/or visual means, e.g., the algorithm may also include steps or functions for generating a variety of autonomic nervous system profile graphs, plots, etc.

The algorithm may be configured to, or otherwise be capable of, directing a microprocessor to activate, i.e., turn "on" and "off" a drug delivery device, e.g., an implantable or external drug delivery device and/or an electrical energy supplying device for applying energy to at least a part of the autonomic nervous system, e.g., in response to the above-described determination of the state of the autonomic nervous system. For example, if it is determined that sympathetic and/or parasympathetic activity needs to be increased or decreased, the processor may direct a drug delivery device to provide the appropriate amount of drug or otherwise execute a suitable drug treatment regime to result in the desired action. Likewise, in embodiments employing electrical modulation, if it is determined that sympathetic and/or parasympathetic activity needs to be increased or decreased, the processor may direct an electrical energy supplying device to provide the appropriate electric impulse or otherwise execute a suitable electric energy treatment regime to result in the desired action The subject invention may also include a data set of known or reference information stored on a computer readable medium to which autonomic nervous system data collected may be compared for use in determining the state of the autonomic nervous system. The data may be stored or configured in a variety of arrangements known to those of skill in the art.

Kits

Also provided are kits for practicing the subject methods. The subject kits may vary greatly in regards to the components included. Embodiments may include one or more pharmacological agents and/or electrical energy supplying devices. In those embodiments that include one or more pharmacological agents, the amount of the pharmacological agents provided in a kit may be sufficient for a single application or for multiple applications. Accordingly, in certain embodiments of the subject kits a single dosage unit of at least one pharmacological agent may be present for a single application.

In certain other embodiments, multiple dosage units of one or more pharmacological agents may be present in a kit for multiple applications. In those embodiments having multiple dosage units, such may be packaged in a single container, e.g., a single tube, bottle, vial, and the like, or one or more dosage units may be individually packaged such that certain kits may have more than one container of a pharmacological agent or of different pharmacological agents.

A kit may include a monthly pack that includes daily discrete or continuous unit doses wherein the total number of daily units present in the monthly pack and may be equal to the total number of days of a month or the days of the menstrual cycle, e.g., a monthly pack may include a minimum of about 30 to about 90 days, e.g., about 30 to about 84 days. The pack may include, for example daily unit doses in the form of oral dosage forms such as tablets, capsules and the like. The monthly pack may be a two or more stage pharmaceutical pack, e.g., containing at least about 30 daily unit doses in two stages. In its first stage, such a pack may include a first pharmaceutical agent or placebo, wherein the first stage includes a minimum of about 25 and a maximum of about 77 daily discrete or continuous doses, e.g., equal to the number of days of one or more particular menstrual cycle phases. The second stage may include a second pharmaceutical agent equal to the number of days of one or more particular menstrual cycle phases (e.g., the luteal phase and/or menses phase), e.g., 5, 6 or 7 daily discrete or continuous unit doses. The first and second pharmaceutical agents may differ in one or more respects, e.g., they may be different pharmaceutical agents (different types), they may be the same pharmaceutical agent but may differ in dose of active agent, etc. More stages may be included in certain embodiments. Accordingly, the monthly pack may include a number of pills to be administered by a subject each day of the month or of the menstrual cycle wherein the pack is configured to include certain pills to be administered to a subject on certain days or during certain menstrual cycle phases, where the type, dosage, etc. of the pills of the pack may vary.

Suitable means for delivering one or more pharmacological agents to a subject may also be provided in a subject kit. The particular delivery means provided in a kit may be dictated by the particular pharmacological agent employed, as describe above, e.g., the particular form of the agent such as whether the pharmacological agent is formulated into preparations in solid, semi-solid, liquid or gaseous forms, such as tablets, capsules, powders, granules, ointments, solutions, suppositories, injections, inhalants and aerosols, and the like, and the particular mode of administration of the agent, e.g., whether oral, buccal, rectal, parenteral, intravaginal, endocervical, intrathecal, intranasal, intravesicular, on the eye, in the ear canal, intraperiactivityal, intradermal, transdermal, intracheal, etc. Accordingly, certain systems may include a suppository applicator, syringe, I.V. bag and tubing, electrode, transdermal patch or film, etc.

Kits may also include diagnostic or detection tests for detecting the occurrence or onset of a particular phase of a subject's menstrual cycle, e.g., by determining certain hormone levels, including relative hormone levels. For example, a urine leutinizing hormone ("LH") detection test or kit or the like may be present in a kit, where such urine LH detection kits are known in the art, e.g., OVUQUICK ONE-STEP, CLEARPLAN EASY and SURESTEP brand detection tests.

Kits may include an electrical energy supplying device, as described above. Accordingly, subject kits may include an energy supplying device such that they may include at least one electrode for electrically modifying at least a portion of a subject's autonomic nervous system in accordance with the subject invention, as described above. In certain embodiments, the energy supplying device provided in a kit is an implantable device, or at least certain components such as one or more electrodes, may be implantable. Certain kits may include a plurality of electrodes, where some or all may be the same or some or all may be different. For example, certain kits may include at least a first electrode for electrically modulating activity at least a portion of the sympathetic system and at least a second electrode for electrically modulating activity in at least a portion of the parasympathetic system. In certain embodiments, a subject kit may include a "test" electrode, as described above such as a radiofrequency controlled electrode. Still further, one or more electrodes may be included in a kit which, instead of or in addition to delivering electric impulses to at least a portion of the autonomic nervous system, delivers an autonomic nervous system pharmacological agent to at least a portion of the autonomic nervous system. Kits according to the subject invention typically also include an energy source such as a battery or generator, where in certain embodiments the energy source may be implantable, and may also include one or more leads or wires for coupling the one or more electrodes to an energy source.

Devices for delivering, e.g., implanting, an electrical energy supplying device and/or a drug delivery device to a target site of a subject such as into the body cavity of a subject may also be included in the subject kits. For example, an endoscope, introducer needle, and the like may be provided.

The subject kits may also include instructions for how to practice the subject methods. For example, instructions may include how to administer the one or more pharmaceutical agents provided in the kit to treat a subject for a condition by pharmacologically modulating at least a portion of the subject's autonomic nervous system. Instructions may include how to use an energy supplying device provided in the kit to treat a subject for a condition by electrically modulating at least a portion of the subject's autonomic nervous system. The instructions are generally recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

It is evident from the above discussion that the above described invention provides methods, system and kits for treating a subject for a condition that is at least suspected of being exacerbated during one or more menstrual cycle phases, e.g., a condition that has catamenial variations. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of treating a female subject for a menopausal mood disorder or premenstrual mood disorder, said method comprising:
    modulating at least a portion of the autonomic nervous system of said subject during the luteal phase of the subject's menstrual cycle to increase the parasympathetic activity/sympathetic activity ratio in a manner effective to treat said subject for said menopausal mood disorder or premenstrual mood disorder, wherein said modulating comprises (a) applying electrical energy during the luteal phase of the subject's menstrual cycle to said at least one portion of said autonomic nervous system by transcutaneous electrical nerve stimulation ("TENS") or (b) administering an effective amount of at least one beta blocker to said subject during the luteal phase of the subject's menstrual cycle;
    so that said subject is treated for said menopausal mood disorder or premenstrual mood disorder, wherein said menopausal mood disorder or premenstrual mood disorder is caused by an abnormal decrease in said parasympathetic activity/sympathetic activity ratio during said luteal phase,
    and wherein said method further comprises determining said parasympathetic activity/sympathetic activity ratio at least one time during said luteal phase of said menstrual cycle.

2. The method of claim 1, wherein said method comprises increasing parasympathetic activity.

3. The method of claim 1, wherein said method comprises decreasing sympathetic activity.

4. The method of claim 1, wherein said method comprises increasing parasympathetic activity and decreasing sympathetic activity.

5. The method of claim 1, wherein said modulating comprises applying electrical energy to at least one portion of said autonomic nervous system.

6. The method of claim 5, wherein said application of electrical energy comprises electrically increasing activity in at least one portion of the parasympathetic nervous system.

7. The method of claim 5, wherein said application of electrical energy comprises electrically inhibiting activity in at least one portion of the sympathetic nervous system.

8. The method of claim 1, wherein said modulating is accomplished by administering an effective amount of at least one beta-blocker to said subject.

9. The method of claim 8, wherein said method comprises increasing said parasympathetic activity/sympathetic activity ratio.

10. The method of claim 1, further comprising performing said modulation of said at least one portion of the autonomic nervous system based on said determined parasympathetic activity/sympathetic activity ratio.

11. The method of claim 1, wherein said luteal phase is the late luteal phase.

12. The method according to claim 2, wherein said increasing parasympathetic activity comprises increasing activity in at least one parasympathetic nerve fiber.

13. The method according to claim 3, wherein said decreasing sympathetic activity comprises decreasing activity in at least one sympathetic nerve fiber.

14. The method according to claim 4, wherein said increasing parasympathetic activity comprises increasing activity in at least one parasympathetic nerve fiber.

15. The method according to claim 4, wherein said decreasing sympathetic activity comprises decreasing activity in at least one sympathetic nerve fiber.

16. The method according to claim 7, wherein said increasing activity in at least one portion of the parasympathetic nervous system comprises increasing activity in at least one parasympathetic nerve fiber.

17. The method according to claim 7, wherein said inhibiting activity in at least one portion of the sympathetic nervous system comprises inhibiting activity in at least one sympathetic nerve fiber.

18. The method according to claim 1, wherein said determining said parasympathetic activity/sympathetic activity ratio comprises determining heart rate variability (HRV) as an indicator of a parasympathetic/sympathetic activity ratio.

19. The method according to claim 1, wherein said determining said parasympathetic activity/sympathetic activity ratio comprises determining respiratory sinus arrhythmia as an indicator of a parasympathetic/sympathetic activity ratio.

20. The method according to claim 1, wherein said determining said parasympathetic activity/sympathetic activity ratio comprises determining an LF/HF ratio as an indicator of a parasympathetic/sympathetic activity ratio.

21. The method of claim 1, wherein said method further comprises a control feedback loop.

22. The method of claim 21, wherein said control feedback loop is an open-loop control system.

23. The method of claim 21, wherein said control feedback loop is a closed-loop control system.

24. The method of claim 21, wherein said control feedback loop comprises determining heart rate variability (HRV).

25. The method of claim 21, wherein said control feedback loop comprises determining respiratory sinus arrhythmia.

26. The method of claim 21, wherein said control feedback loop comprises determining an LF/HF ratio.

27. The method of claim 1, further comprising determining the occurrence of said luteal phase of said subject's menstrual cycle.

28. The method of claim 1, wherein said administering is throughout all of said luteal phase.

29. A method of treating a female subject for a menopausal mood disorder or premenstrual mood disorder, said method consisting of:

modulating at least a portion of the autonomic nervous system of said subject during the luteal phase of the subject's menstrual cycle to increase the parasympathetic activity/sympathetic activity ratio in a manner effective to treat said subject for said menopausal mood disorder or premenstrual mood disorder, wherein said modulating comprises (a) applying electrical energy during the luteal phase of the subject's menstrual cycle to said at least one portion of said autonomic nervous system by transcutaneous electrical nerve stimulation ("TENS") or (b) administering an effective amount of at least one beta blocker to said subject during the luteal phase of the subject's menstrual cycle;

so that said subject is treated for said menopausal mood disorder or premenstrual mood disorder, wherein said menopausal mood disorder or premenstrual mood disorder is caused by an abnormal decrease in said parasympathetic activity/sympathetic activity ratio during said luteal phase, and wherein said method further comprises determining said parasympathetic activity/sympathetic activity ratio at least one time during said luteal phase of said menstrual cycle.

* * * * *

UNITED STATES PATENT AND TRADEMARK OFFICE
CERTIFICATE OF CORRECTION

| | | |
|---|---|---|
| PATENT NO. | : 7,899,527 B2 | |
| APPLICATION NO. | : 10/846486 | |
| DATED | : March 1, 2011 | |
| INVENTOR(S) | : Anthony Joonkyoo Yun | |

It is certified that error appears in the above-identified patent and that said Letters Patent is hereby corrected as shown below:

In Claim 16 (Original Claim 71), Section 56, line 31, replace the words "claim 7" with the words claim 6.

Signed and Sealed this
Eleventh Day of September, 2012

David J. Kappos
*Director of the United States Patent and Trademark Office*